US012117442B2

(12) United States Patent
Hamilton et al.

(10) Patent No.: US 12,117,442 B2
(45) Date of Patent: Oct. 15, 2024

(54) METHODS OF SCREENING COMPOUNDS

(71) Applicant: Depixus SAS, Paris (FR)

(72) Inventors: Gordon Hamilton, Sevres (FR); Jimmy Ouellet, Lardy (FR); Zhen Wang, Paris (FR); Henning Labuhn, Paris (FR)

(73) Assignee: Depixus SAS, Paris (FR)

( * ) Notice: Subject to any disclaimer, the term of this patent is extended or adjusted under 35 U.S.C. 154(b) by 0 days.

(21) Appl. No.: 18/339,347

(22) Filed: Jun. 22, 2023

(65) Prior Publication Data

US 2023/0375542 A1 Nov. 23, 2023

Related U.S. Application Data

(63) Continuation of application No. PCT/IB2023/053283, filed on Mar. 31, 2023.

(60) Provisional application No. 63/326,370, filed on Apr. 1, 2022.

(51) Int. Cl.
*G01N 33/53* (2006.01)
*G01N 33/543* (2006.01)

(52) U.S. Cl.
CPC ... *G01N 33/54373* (2013.01); *G01N 33/5308* (2013.01); *G01N 33/54326* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 9,933,609 | B2 | 4/2018 | Croquette |
| 10,209,505 | B2 | 2/2019 | Croquette |
| 10,933,416 | B2 | 3/2021 | Croquette |
| 2018/0291434 | A1 | 10/2018 | Wong |

FOREIGN PATENT DOCUMENTS

| | | | |
|---|---|---|---|
| EP | 2948774 | B1 | 7/2018 |
| EP | 3181703 | B1 | 12/2018 |
| EP | 3505641 | A1 | 7/2019 |
| EP | 3914949 | A1 | 12/2021 |
| EP | 3990958 | A1 | 5/2022 |
| EP | 3803492 | B1 | 8/2022 |
| WO | 2016177869 | A1 | 11/2016 |

OTHER PUBLICATIONS

Mustafa et al (Biosensors and Bioelectronics 121:34-40) (Year: 2018).*

Mustafa et al (Biosensors and Bioelectronics 121:34-40 supplementary materials) (Year: 2018).*

Iida et al (Chemical Record 13:539-48) (Year: 2013).*

Kim et al (JACS 124:2098-9) (Year: 2002).*

Ding, F., et al., "Single-molecule mechanical identification and sequencing" Nat Methods. Mar. 11, 2012;9(4):367-72. doi: 10.1038/nmeth.1925.

Salerno, D., et al., "Magnetic tweezers measurements of the nanomechanical properties of DNA in the presence of drugs" Nucleic Acids Res. Nov. 2010;38(20):7089-99. doi: 10.1093/nar/gkq597.

Skinner, G.M., et al., "Single-molecule techniques for drug discovery" Assay Drug Dev Technol. Aug. 2004;2(4):397-405. doi: 10.1089/adt.2004.2.397.

Aboul-Ela, F. & Varani, G. Recognition of HIV-1 TAR RNA by Tat protein and Tat-derived peptides. Journal of Molecular Structure: THEOCHEM 423, 29-39 (1998).

Abulwerdi, F.A., et al., "Development of Small Molecules with a Noncanonical Binding Mode to HIV-1 Trans Activation Response (TAR) RNA" J Med Chem. Dec. 22, 2016;59(24):11148-11160. doi: 10.1021/acs.jmedchem.6b01450.

Blount, K.F., et al., "Using pyrene-labeled HIV-1 TAR to measure RNA-small molecule binding" Nucleic Acids Res. Oct. 1, 2003;31(19):5490-500. doi: 10.1093/nar/gkg755.

Brodsky, A.S., et al., "Solution structure of the HIV-2 TAR-argininamide complex" J Mol Biol. Apr. 4, 1997;267(3):624-39. doi: 10.1006/jmbi.1996.0879.

Chavli, S.S., et al., "Face-time with TAR: Portraits of an HIV-1 RNA with diverse modes of effector recognition relevant for drug discovery" J Biol Chem. Jun. 14, 2019;294(24):9326-9341. doi: 10.1074/jbc.REV119.006860. Epub May 12, 2019.

Connelly, C.M., et al., "The Emerging Role of RNA as a Therapeutic Target for Small Molecules" Cell Chem Biol. Sep. 22, 2016;23(9):1077-1090. doi: 10.1016/j.chembiol.2016.05.021. Epub Sep. 1, 2016.

Costales, M.G., et al., "How We Think about Targeting RNA with Small Molecules" J Med Chem. Sep. 10, 2020;63(17):8880-8900. doi: 10.1021/acs.jmedchem.9b01927. Epub Mar. 26, 2020.

Di Gorgio, A., et al., "Synthetic small-molecule RNA ligands: future prospects as therapeutic agents" Medchemcomm. Apr. 30, 2019;10(8):1242-1255. doi: 10.1039/c9md00195f.

Dingwall, C., et al., "HIV-1 tat protein stimulates transcription by binding to a U-rich bulge in the stem of the TAR RNA structure" EMBO J. Dec. 1990;9(12):4145-53. doi: 10.1002/j.1460-2075.1990.tb07637.x.

(Continued)

*Primary Examiner* — Christopher M Gross
(74) *Attorney, Agent, or Firm* — Greenberg Traurig, LLP

(57) ABSTRACT

Disclosed herein are methods of screening candidate binding compounds to a plurality of target nucleic acids either of the same sequence or of different sequences utilizing a device configured to detect changes in the folding and unfolding force of the target nucleic acid upon binding to various candidate binding compounds. In the presence of a plurality of nucleic acid sequences, the methods described herein also can rapidly determine the specificity of the small molecule or polypeptide to a nucleic acid structure. Also, disclosed herein are methods of measuring binding kinetics of binding compounds to a target nucleic acid using a device configured to detect changes in the folding and unfolding force of the target nucleic acid upon binding to varying concentrations of the candidate binding compound.

18 Claims, 20 Drawing Sheets

Specification includes a Sequence Listing.

(56) References Cited

OTHER PUBLICATIONS

Eichhorn, C.D., et al., “Structure and function of preQ1 riboswitches” Biochim Biophys Acta. Oct. 2014;1839(10):939-950. doi: 10.1016/j.bbagrm.2014.04.019.
Zhang, Q., et al., “Comparison of solution and crystal structures of preQ1 riboswitch reveals calcium-induced changes in conformation and dynamics” J Am Chem Soc. Apr. 13, 2011;133(14):5190-3.
Eichhorn, C.D., et al., “Unraveling the structural complexity in a single-stranded RNA tail: implications for efficient ligand binding in the prequeuosine riboswitch” Nucleic Acids Res. Feb. 2012;40(3):1345-55. doi: 10.1093/nar/gkr833.
ENCODE Project Consortium. An integrated encyclopedia of DNA elements in the human genome. Nature. Sep. 6, 2012;489(7414):57-74. doi: 10.1038/nature11247.
Feng, J., et al., “Cooperative and directional folding of the preQ1 riboswitch aptamer domain” J Am Chem Soc. Mar. 30, 2011;133(12):4196-9. doi: 10.1021/ja110411m.
Filipowicz, W., et al., “Mechanisms of post-transcriptional regulation by microRNAs: are the answers in sight?” Nat Rev Genet. Feb. 2008;9(2):102-14.
Gong, Z. et al., “Insights into ligand binding to PreQ1 Riboswitch Aptamer from molecular dynamics simulations” PLoS One. Mar. 24, 2014;9(3):e92247. doi: 10.1371/journal.pone.0092247.
Gong, Z., et al., “Computational study of unfolding and regulation mechanism of preQ1 riboswitches” PLoS One. 2012;7(9):e45239. doi: 10.1371/journal.pone.0045239.
Ha, M. & Kim, V. N., “Regulation of microRNA biogenesis” Nature Reviews Molecular Cell Biology 15, 509-524 (2014).
Haniff, H., et al., “Target-Directed Approaches for Screening Small Molecules against RNA Targets” SLAS Discov. Sep. 2020;25(8):869-894. doi: 10.1177/2472555220922802.
Kang, M.et al., “Structural Insights into riboswitch control of the biosynthesis of queuosine, a modified nucleotide found in the anticodon of tRNA” Mol Cell. Mar. 27, 2009;33(6):784-90. doi: 10.1016/j.molcel.2009.02.019.
Klein, D.J., et al., “Cocrystal structure of a class I preQ1 riboswitch reveals a pseudoknot recognizing an essential hypermodified nucleobase” Nat Struct Mol Biol. Mar. 2009;16(3):343-4.
Kumarswamy, R., et al., “Regulation and function of miRNA-21 in health and disease” RNA Biol. Sep.-Oct. 2011;8(5):706-13. doi: 10.4161/rna.8.5.16154.
Li, P.T.X, et al., “Probing the mechanical folding kinetics of TAR RNA by hopping, force-jump, and force-ramp methods” Biophys J. Jan. 1, 2006;90(1):250-60. doi: 10.1529/biophysj.105.068049. Epub Oct. 7, 2005.
Liu, Z., et al., “Structure of Human Dicer and Its Complexes with a Pre-miRNA Substrate” Cell. May 17, 2018;173(5):1191-1203.e12. doi: 10.1016/j.cell.2018.03.080.
Montange, R. K., et al., “Riboswitches: emerging themes in RNA structure and function” Annu Rev Biophys. 2008;37:117-33. doi: 10.1146/annurev.biophys.37.032807.
Morris, R.C., et al., “Queuosine modification of tRNA: a case for convergent evolution” Mol Genet Metab. Sep.-Oct. 2001;74(1-2):147-59. doi: 10.1006/mgme.2001.3216.
Provost, P., et al., “Ribonuclease activity and RNA binding of recombinant human Dicer” EMBO J. Nov. 1, 2002;21(21):5864-74. doi: 10.1093/emboj/cdf578.
Puglisi, J.D., et al., “Role of RNA structure in arginine recognition of TAR RNA” Proc Natl Acad Sci U S A. Apr. 15, 1993;90(8):3680-4. doi: 10.1073/pnas.90.8.3680.
Roth, A., et al., “A riboswitch selective for the queuosine precursor preQ1 contains an unusually small aptamer domain” Nat Struct Mol Biol. Apr. 2007;14(4):308-17. doi: 10.1038/nsmb1224.
Roy, S., et al., “A bulge structure in HIV-1 TAR RNA is required for Tat binding and Tat-mediated trans-activation” Genes Dev. Aug. 1990;4(8):1365-73. doi: 10.1101/gad.4.8.1365.
Stelzer, A.C., et al., “Discovery of selective bioactive small molecules by targeting an RNA dynamic ensemble” Nat Chem Biol. Jun. 26, 2011;7(8):553-9. doi: 10.1038/nchembio.596. PMID: 21706033.
Suddala, K.C., et al., “Single transcriptional and translational preQ1 riboswitches adopt similar pre-folded ensembles that follow distinct folding pathways into the same ligand-bound structure” Nucleic Acids Res. Dec. 2013;41(22):10462-75. doi: 10.1093/nar/gkt798.
Suresh, B.M., et al., “A general fragment-based approach to identify and optimize bioactive ligands targeting RNA” Proc Natl Acad Sci U S A. Dec. 29, 2020;117(52):33197-33203. doi: 10.1073/pnas.2012217117.
Sztuba-Solinska, J. et al., “Identification of biologically active, HIV TAR RNA-binding small molecules using small molecule microarrays” J Am Chem Soc. Jun. 11, 2014;136(23):8402-10. doi: 10.1021/ja502754f. Epub May 28, 2014.
Tinoco, I., et al., “The effect of force on thermodynamics and kinetics: unfolding single RNA molecules” Biochem Soc Trans. Nov. 2004;32(Pt 5):757-60. doi: 10.1042/BST0320757.
Wang, Z., et al., Detection of genetic variation and base modifications at base-pair resolution on both DNA and RNA: Commun Biol. Jan. 29, 2021;4(1):128. doi: 10.1038/s42003-021-01648-7. Erratum in: Commun Biol. Mar. 11, 2021;4(1):346.
Warner, K.D., et al., Principles for targeting RNA with drug-like small molecules. Nat Rev Drug Discov. Aug. 2018;17(8):547-558. doi: 10.1038/nrd.2018.93. Epub Jul. 6, 2018.
Yu, A.M., “RNA Drugs and RNA Targets for Small Molecules: Principles, Progress, and Challenges” Pharmacol Rev. Oct. 2020;72(4):862-898. doi: 10.1124/pr.120.019554.

* cited by examiner

METHODS OF SCREENING COMPOUNDS

CROSS-REFERENCED APPLICATION

This application is a continuation of International Application No PCT/IB2023/0523283, filed Mar. 31, 2023, which claims the benefit of priority to U.S. Provisional Application No. 63/326,370, filed on Apr. 1, 2022, the entire contents of each of which are incorporated herein by reference.

INCORPORATION BY REFERENCE OF SEQUENCE LISTING

The instant application contains a Sequence Listing, which has been submitted via Patent Center. The Sequence Listing titled 201326.701601_PCT_SL.xml, which was created on Mar. 31, 2023, and is 43,892 bytes in size, is hereby incorporated by reference in its entirety.

FIELD

The present disclosure relates generally to methods kits for identifying candidates that are capable of interacting with a nucleic acid, a protein or an analog thereof.

BACKGROUND

Candidates that can bind to target molecule can be identified by high throughput screening. High throughput screening allows to test thousands to millions of molecules using automated equipment. To identify candidates, one strategy consists of identifying high quality hits first, and then affine the selection for example, by modifying high quality hits to design candidates. In parallel, it is also possible to test various doses of selected candidates to reach a quantitative analysis of molecules' behavior and potentially predict their activity.

To improve the selection of these potential candidates, and/or to get more meaningful results, several methods have been developed such as the very sensitive optical method "Surface Plasmon Resonance (SPR)". SPR occurs when polarized light strikes an electrically conducting surface at the interface between two media. This generates electron charge density waves called plasmons, reducing the intensity of reflected light at a specific angle known as the resonance angle, in proportion to the mass on a sensor surface. This technique allows therefore to detect molecular interactions in real time. However, this still relies on the binding between molecules only. Attempts have been made, for identifying methods to improve the accuracy for selecting candidates but methods used remain challenging. Therefore, there is still a need for devices and methods for a faster, more selective and accurate detection of a new candidate acting on a nucleic acid or a protein.

SUMMARY

Disclosed herein are methods of screening or identifying binding molecules to a conformational structure of a nucleic acid molecule, in real time.

In some embodiments, the method comprises: (a) attaching a plurality of the nucleic acid molecules to a plurality of beads via one end of the nucleic acid molecule; (b) attaching a plurality of nucleic acid molecules to a plurality of features of a device via a second end of the nucleic acid molecule, (c) contacting a chamber with a library of binding molecules, wherein each member of the library of binding molecules are contacted with a plurality of single nucleic acid molecule in a single chamber; (d) approaching a magnet to cause the plurality of beads to move relative to a bottom surface along an axis of the chamber and measuring a change in bead position via a sensor of the device based on movement of the bead relative to the bottom surface, (e) determining an unfolding force of the nucleic acid molecule in the presence of each member of the library of binding molecules; (f) selecting members of the library of binding molecules that produce an unfolding force of the nucleic acid molecule that is greater or smaller than an unfolding force of the nucleic acid molecule in the absence of the binding molecule; and (g) optionally, testing the activity of the identified binding molecule, as a medicament. In some embodiments, the plurality of features comprises at least 10,000 features. In some embodiments, the sensor of (d) comprises a camera CMOS capable of collecting photons reflected from the beads. In some embodiments, the sensor of (d) comprises a CMOS capable of measuring impedance from the features caused by the movement of the beads up and down. In some embodiments, the nucleic acid molecule is a DNA molecule. In some embodiments, the nucleic acid molecule is an RNA molecule. In some embodiments, the nucleic acid molecule is a DNA/RNA hybrid molecule. In some embodiments, the plurality of nucleic acid molecules are the same nucleic acid molecules. In some embodiments, the plurality of nucleic acid molecules are different nucleic acid molecules. In some embodiments, a force of the magnet relative to the bead is constant. In some embodiments, a force of the magnet relative the bead is increased. In some embodiments, the nucleic acid molecule is from about 20 bp to about 350 bp. In some embodiments, the nucleic acid molecule is more than 20 bp and up to more than 1.5 kb. In some embodiments, the nucleic acid molecule is from about 20 bases to about 350 bases. In some embodiments, the nucleic acid molecule is more than 20 bases and up to more than 1.5 bases. In some embodiments, the nucleic acid molecule is chemically synthesized. In some embodiments, the nucleic acid molecule is produced via in vitro transcription. In some embodiments, the nucleic acid molecule is produced via polymerase chain reaction. In some embodiments, the nucleic acid molecule(s) is (are) purified from at least one cell and may be compared to the nucleic acid from a sick (cancer) cell. In some embodiments, the binding molecule is a small molecule. In some embodiments, the binding molecule is a polypeptide. In some embodiments, the device is configured to resolve a difference in unfolding force of from about 0.1 fold to about 30-fold among members of the library of binding molecules. In some embodiments, the attaching of (a) comprises a biotin-streptavidin binding, wherein the biotin is conjugated onto one end of the nucleic acid and the streptavidin is conjugated onto the bead. In some embodiments, the attaching of (b) comprises a DNA oligonucleotide covalently attached to the bottom of each feature, wherein the DNA oligonucleotide has complementarity to the second end of the nucleic acid molecule.

In some embodiments, the method further comprises a step of contacting the nucleic acid, with and analyzing the binding of a small molecule, a protein such as an enzyme interacting with said nucleic acid. In some embodiments, the nucleic acid comprises (or is, or consists of) an aptamer.

Also disclosed herein are methods of identifying a chemical signature of optimal binders among a library of binding molecules to a nucleic acid molecule. In some embodiments, the method comprises: (a)attaching a plurality of the nucleic acid molecules to a plurality of beads via a first end of the nucleic acid molecule; (b) attaching a plurality of nucleic acid molecules to a plurality of features of a device via a second end of the nucleic acid molecule; (c) contacting a chamber with a library of binding molecules, wherein each member of the library of binding molecules are contacted with a single nucleic acid molecule; (d) approaching a magnet to cause the plurality of beads to move relative to a bottom surface along an axis of the chamber and measuring a change in bead position via a sensor of the device based on movement of the bead relative to the bottom surface; (e) determining an unfolding force of the nucleic acid molecule in the presence of each member of the library of binding molecules; (f) selecting members of the library of binding molecules that produce an unfolding force of the nucleic acid molecule that is greater or smaller than an unfolding force of the nucleic acid molecule in the absence of the binding molecule; and (g) modeling the selected members of the library of binding molecules to identify a chemical signature of optimal binders among the library of binding molecules. In some embodiments, the plurality of features comprises at least 10,000 features. In some embodiments, the sensor of (d) comprises a camera CMOS capable of collecting photons reflected from the beads. In some embodiments, the sensor of (d) comprises a CMOS capable of measuring impedance from the features caused by the movement of the beads up and down. In some embodiments, the nucleic acid molecule is a DNA molecule. In some embodiments, the nucleic acid molecule is an RNA molecule. In some embodiments, the nucleic acid molecule is a DNA/RNA hybrid molecule. In some embodiments, the plurality of nucleic acid molecules are the same nucleic acid molecules. In some embodiments, the plurality of nucleic acid molecules are different nucleic acid molecules. In some embodiments, a force of the magnet relative to the bead is constant. In some embodiments, a force of the magnet relative the bead is increased. In some embodiments, the nucleic acid molecule is from about 20 bp to about 350 bp. In some embodiments, the nucleic acid molecule is from about 20 bases to about 350 bases. In some embodiments, the nucleic acid molecule is chemically synthesized. In some embodiments, the nucleic acid molecule is produced via in vitro transcription. In some embodiments, the nucleic acid molecule is produced via polymerase chain reaction. In some embodiments, the nucleic acid molecule(s) is (are) purified from a cell. In some embodiments, the binding molecule is a small molecule. In some embodiments, the binding molecule is a polypeptide. In some embodiments, the device is configured to resolve a difference in unfolding force of from about 0.1 fold to about 30-fold among members of the library of binding molecules. In some embodiments, the attaching of (a) comprises a biotin-streptavidin binding, wherein the biotin is conjugated onto one end of the nucleic acid and the streptavidin is conjugated onto the bead. In some embodiments, the attaching of (b) comprises a DNA oligonucleotide covalently attached to the bottom of each feature, wherein the DNA oligonucleotide has complementarity to the second end of the nucleic acid molecule.

Also disclosed herein are methods of determining binding kinetics of a binding molecule to a nucleic acid molecule. In some embodiments, the method comprises: (a) attaching a plurality of the nucleic acid molecules to a plurality of beads via a first end of the nucleic acid molecule; (b) attaching a plurality of nucleic acid molecules to a plurality of features of a device via a second end of the nucleic acid molecule; (c) contacting a chamber with increasing concentrations of the binding molecule; (d) applying a magnetic field sufficient to cause each bead of the plurality of beads to move relative to a bottom surface of the chamber and measuring a change in bead position via a sensor of the device based on movement of the bead relative to the bottom surface; (e) determining an unfolding force of the nucleic acid molecule as a function of the concentration of the binding molecule; and (f) calculating the binding kinetics of the binding molecule to the nucleic acid molecule based on the change unfolding force as a function of the amount of the binding molecule. In some embodiments, the unfolding force of the nucleic acid molecule as a function of the concentration of the binding molecule is calculated for each concentration of the binding molecule simultaneously. In some embodiments, the binding molecule has a dissociation constant ($K_D$) of from about 0.01 nM to about 100 mM.

Also disclosed herein are methods of determining binding kinetics of a binding molecule to a nucleic acid molecule. In some embodiments, the methods comprise: (a) contacting the nucleic acid molecule attached to a fixed end of a chamber and a magnetic bead on opposite ends with increasing concentrations of the binding molecule; and (b) determining an unfolding force of the nucleic acid as a function of the concentration of the binding molecule, wherein the nucleic acid molecule is selected from the group consisting of: HIV-1 TAR, preQ1 riboswitch, pre-miR-21, MYC, APOC3, DM1, C9orf72, MAPT, and FMR1. In some embodiments, the binding molecule is a small chemical molecule. In some embodiments, the binding molecule is a polypeptide. In some embodiments, the binding molecule has a dissociation constant ($K_D$) of from about 0.01 nM to about 100 mM. In some embodiments, the chamber is disposed in a device configured to measure the displacement of a bead of the nucleic acid as a function of the concentration of the binding molecule. In some embodiments, the device comprises a plurality of features. In some embodiments, a plurality of nucleic acid molecules is anchored to a bottom of the plurality of features, wherein each feature of a chamber comprises a single nucleic acid molecule sequence among the plurality of nucleic acid molecule sequences. In some embodiments, a single concentration of the binding molecule is added to the chamber, and wherein the unfolding force of the nucleic acid as a function of the concentration of the binding molecule is calculated for each concentration of the binding molecule. In some embodiments, the plurality of features comprises at least 10,000 features. In some embodiments, the nucleic acid molecule is HIV-1 TAR. In some embodiments, the nucleic acid molecule is preQ1 riboswitch. In some embodiments, the preQ1 riboswitch comprises a mutation, relative to a wild type preQ1 riboswitch, that is selected from the group consisting of: C15U, U7C, A10G, and U6C. In some embodiments, the nucleic acid molecule is pre-miR-21. In some embodiments, the nucleic acid molecule is DM1.

In some embodiments, the nucleic acid molecule is a viral nucleic acid, a nucleic acid isolated from a bacteria, preferably isolated from a pathogenic viral agent or from a pathogenic bacterial agent. In some embodiments, the nucleic acid is from a cell isolated from a cancer, or under pathological stress. In some embodiments, the nucleic acid molecule is a viral RNA isolated from a RNA virus. In some embodiments, the viral RNA is from a corona virus. In some embodiments, the viral RNA is from a SARS virus, MERS virus, or SARS-COV-2 virus.

Also disclosed herein are systems for practicing the methods disclosed herein; kits and containers comprising the systems disclosed herein; and apparatuses comprising the systems or devices disclosed herein. In some embodiments, the invention also provides a system or a device for selecting a molecule(s) binding to a conformational state of a nucleic acid in real time.

Also disclosed herein are systems for screening binding molecules to a nucleic acid molecule. In some embodiments, the system comprises: (a) a plurality of the nucleic acid molecules attached to a plurality of beads via one end of the nucleic acid molecule; (b) a plurality of nucleic acid molecules attached to a plurality of features of a device via a second end of the nucleic acid molecule; (c) a chamber with a library of binding molecules, wherein each member of the library of binding molecules are contacted with a plurality of single nucleic acid molecule in a single chamber; (d) a magnet to cause the plurality of beads to move relative to a bottom surface along an axis of the chamber; and (e) a sensor to measure a change in bead position of the device based on movement of the bead relative to the bottom surface.

Also disclosed herein are systems for determining the binding kinetics of a binding molecule to a nucleic acid molecule. In some embodiments, the system comprises: (a) a plurality of the nucleic acid molecules attached to a plurality of beads via one end of the nucleic acid molecule; (b) a plurality of nucleic acid molecules attached to a plurality of features of a device via a second end of the nucleic acid molecule; (c) a chamber with a library of binding molecules, wherein each member of the library of binding molecules are contacted with a plurality of single nucleic acid molecule in a single chamber; (d) a magnet to cause the plurality of beads to move relative to a bottom surface along an axis of the chamber; and (e) a sensor to measure a change in bead position of the device based on movement of the bead relative to the bottom surface.

Also disclosed herein are kits comprising: (a) a nucleic acid molecule, or a plurality of the same or of different nucleic acid molecules comprising an orienting sequence at one end and a biotin moiety at the other end; (b) a DNA handle comprising a first reactive group, wherein the DNA handle is capable of hybridizing to the orienting sequence; (c) a feature of a device comprising a second reactive group that is capable of undergoing a chemical reaction with the first reactive group; and (d) a bead or a plurality of beads comprising streptavidin moiety that is capable of binding to the biotin moiety. In some embodiments, the kit further comprises a library of binding molecules. In some embodiments, the library of binding molecules comprises a library of small molecules, a library of proteins, a library of antibodies, a library of aptamers, advantageously a library comprising binding molecules. In some embodiments, the kit further comprises a buffer comprising a divalent cation in a range of from 1 μM to 1 mM. In some embodiments, the divalent cation comprises $Mg^{2+}$, $Mn^{2+}$, $Zn^{2+}$, $Fe^{2+}$, $Cu^{2+}$, or $Cd^{2+}$. In some embodiments, the chemical reaction is an esterification reaction. In some embodiments, the chemical reaction is a click chemistry.

BRIEF DESCRIPTION OF THE DRAWINGS

Novel features of exemplary embodiments are set forth with particularity in the appended claims. A better understanding of the features and advantages will be obtained by reference to the following detailed description that sets forth illustrative embodiments, in which the principles of the disclosed systems and methods are utilized, and the accompanying drawings of which:

FIG. 2A illustrates the structure of HIV-1 TAR with nucleotides that interact with a small molecule as provided in Chavali SS, Bonn-Breach R, Wedekind JE. (2019) Face-time with TAR: Portraits of an HIV-1 RNA with diverse modes of effector recognition relevant for drug discovery. J. Biol. Chem. 294:9326-9341. Changes in the unfolding force of the HIV-TAR molecule are depicted in the presence of Argininamide (FIG. 2B), Netilmicin (FIG. 2C), Kanamycin, (FIG. 2D), and Compound 4 (3-Amino-6-methyl-N-[3-(trifluoromethyl)phenyl]thieno[2,3-b]pyridine-2-carboxamide) (FIG. 2E). The number of HIV-TAR molecules (n) analyzed in each condition is shown, and the unfolding force at each cycle is normalized to the median force of each molecule in the control condition. The force at the maximum distribution of each bead is taken and the median force of all beads with s.e.m is shown for each condition. The calculated $K_D$ is shown for each molecule.

FIG. 3A is a schematic representation of the Bsu preQ1 riboswitch in the ligand-bound form, and the proposed molecular folding pathway as provided in Gong Z, Zhao Y, Chen C, Duan Y, Xiao Y (2014) Insights into Ligand Binding to PreQ1 Riboswitch Aptamer from Molecular Dynamics Simulations. PLOS ONE 9(3): e92247. Eichhorn, Catherine D. et al. "Structure and function of preQ1 riboswitches." *Biochimica et biophysica acta* 1839 10 (2014): 939-950. FIG. 3B illustrates the transition between unfolded and folded states of a single preQ1 RNA molecule with increasing concentrations of its ligand preQ1 at 9.6 pN. The trace is fitted with the Hidden Markov model. The RNA is considered bound to a preQ1 when it stays folded for longer than 3.3 s, and between the two bound-states is the time when the RNA is free of preQ1. The attachment rate ($K_{on}$) and the detachment rate ($K_{off}$) can be calculated and the overall $K_D$ at 9.6 pN is 73 nM (n=49). FIG. 3C shows exemplary analysis of the binding kinetic ($k_{on}$ and $k_{off}$) of a preQ1 ligand on a preQ1 RNA secondary structure that is calculated for each trace shown in FIG. 3B. FIG. 3D shows representative binding kinetics curve based on the long constant force experiments for determining $k_{on}$ of a ligand. FIG. 3E shows representative binding kinetics curve based on the long constant force experiments for determining $k_{off}$ of a ligand. FIG. 3F depicts constant-force step of a single preQ1 RNA molecule with increasing concentrations of preQ1. Each step represents a different force, increasing from left to right. FIG. 3G shows a graph in which the transition frequency between folded and unfolded state is plotted against different forces for different preQ1 concentrations. The force is normalized to the median transition force for each bead in control conditions. FIG. 3H depicts a graph showing the unfolding probability at different forces for a single molecule, and the transition force (50% probability of unfolding) can be calculated for different concentrations. FIG. 3I illustrates the inflection half-width for different concentrations. The $K_D$ can be calculated by fitting the inflection force with different preQ1 concentrations. FIG. 3J illustrates the relative unfolding force with PreQ1 and/or $Mg^{2+}$. FIG. 3K illustrates the inflection half-width with PreQ1 and/or $Mg^{2+}$.

FIG. 4A illustrates the effects of Bsu loop mutations on preQ1 binding as provided in Eichhorn, Catherine D. et al. "Structure and function of preQ1 riboswitches." *Biochimica et biophysica acta* 1839 10 (2014): 939-950. The distribution of unfolding forces with increasing concentrations of preQ1 and the $K_D$ fit are illustrated for WT (FIG. 4B), C15U (FIG. 4C), U7C+C15U (FIG. 4D), A10G (FIG. 4E), and U6C (FIG. 4G). FIG. 4F depicts the effect of PreQ1 at different concentrations on the mutant A10G. The unfolding force is normalized to the median force of each bead in control conditions. The fraction of cycles that have unfolding forces greater than the 95% confidence interval for all beads in control condition is calculated for WT, C15U and U7C+C15U mutants and this is what is used to calculate the $K_D$. This threshold force for each molecule is shown (FIGS. 4B-4D). The unfolding force at the maximum distribution for each bead is used for A10G and U6C (FIGS. 4E and 4G). The median of all beads are shown with s.e.m. and the number of beads used are shown as well. The $K_D$ is fitted for each molecule and all obtained values are presented in the table, (n.a.: not applicable).

DETAILED DESCRIPTION

Overview

Provided herein are methods to identify candidates, as a potential medicament for the prevention or the treatment of a disease or a condition directly or indirectly related to said nucleic acid or protein, or an analog thereof. In some embodiments, the methods can be used to identify candidates for use as medication against etiological agents. In some embodiments, the etiological agents comprise a COVID-19 virus or a SARS-COV virus.

In some embodiments, the methods described herein comprises the conformational structure of a target molecule and its capacity for interacting with a candidate in real time. Accordingly, in some embodiments, the methods described herein comprise considering the primary sequence of a molecule, and its structural conformation (folding and/or epigenetic markers) to select binding molecules from a library. This is achieved using a method described herein that can modify the secondary structure of a molecule and, therefore, identify binding to specific "epitopes" or "motifs" related to such secondary structure.

As proteins and nucleic acids have a secondary and 3D structure, that influence their interaction with other molecules, either other nucleic acid(s) or with specific cellular or nuclear constituents. The presence of epigenetic markers that may be silencing or boosting residues, may also influence the capacity of candidate to bind to specific "motifs" of a target nucleic acid (e.g., DNA or RNA). For example, in some embodiments, the epigenetic marker that stamps RNAs, m6A, boosts gene expression needed for embryonic stem cells to properly differentiate into different cell types. But, in some embodiments, the epigenetic marker, m6A, restricts differentiation in blood stem cells. Accordingly, in leukemia—a disease of blood stem cells gone awry—m6A sustains disease by keeping the cells in a stemlike state.

Various conformational structures or foldings of double strand (ds) and single strand (ss) nucleic acids have been identified. Non-limiting examples of the conformational structures include hairpins, P-shape, T-shapes, and candy shape. Access to these conformation structures is complex and brief. Therefore, measuring an interaction of molecules with the conformational structures remain a challenge. Accordingly, provided herein are devices and methods for detecting and selecting compounds that could impact the functioning of such target molecules (e.g., nucleic acids).

Provided herein are methods for detecting changes in the structure of a target molecule (e.g., nucleic acid, protein, or analog thereof). Also provided herein are methods of screening and identifying in a library, wherein the library comprises molecules that bind to the different structural conformations of a nucleic acid, in real time.

Figure 1A:
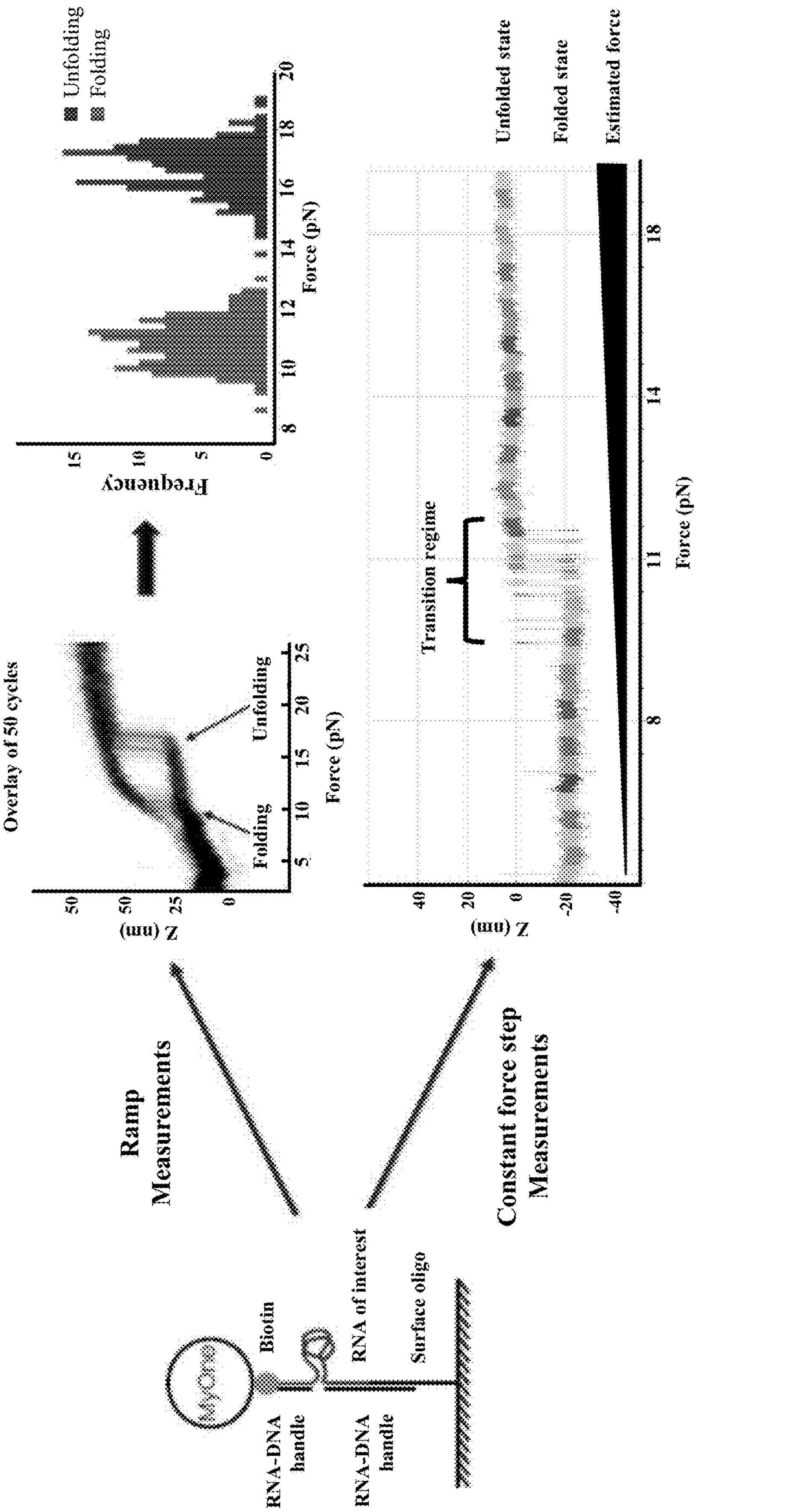
FIG. 1A depicts an exemplary RNA molecule conjugated to a chamber as described herein, which is utilized in ramp experiments (subjected to multiple cycles of increasing and decreasing forces) and constant-force experiments (subjected to the same force for a certain amount of time (e.g., 30 seconds to 2 hours) before increasing the force (e.g., single constant force or stepped constant force)). A single or a stepped constant (ramp) force is applied to the RNA.

In some embodiments, the methods comprise exerting a force at one end of a nucleic acid linked to a support (a feature of a chamber), and thereby detecting changes in the conformational structure of the nucleic acid. For example, in some embodiments, variations in the force required to unfold (or refold) it (nucleic acid) in the presence or absence of binding molecules are detected, Provided herein are methods of screening compounds for binding to a target nucleic acid utilizing a platform described herein. Such methods include immobilizing a target nucleic acid onto a surface of a device by one end, and a magnetic bead on the other end. As shown in FIG. 1A, a DNA handle can be used to immobilize the target RNA to the surface and bead. For example, a feature, e.g., a DNA oligo can be chemically linked to the surface, where the DNA oligo has complementarity to a first end of the target nucleic acid. Next, in step (a), a second DNA oligo conjugated to a biotin moiety and having complementarity to a second end of the target nucleic acid can be added. Alternatively, the biotin is present on the target RNA itself, either at 3' end or at 5' end. Finally, in step (b), a magnetic bead having a streptavidin moiety can be added to immobilize the second end of the target nucleic acid to the magnetic bead. Accordingly, in the method provided, step (b) can be performed before step (a), and both are required.

By providing the immobilized target nucleic acid between the device surface and the magnetic bead, a magnetic force can be applied. One way of immobilizing a target nucleic acid is described in Wang, Z., Maluenda, J., Giraut, L. et al. Detection of genetic variation and base modifications at base-pair resolution on both DNA and RNA. *Commun Biol* 4, 128 (2021) enclosed here by reference in entirety. Application of the magnetic force produces a force along a z-axis perpendicular to the surface of the device. By increasing the magnetic force, the target nucleic acid can be unfolded, and can then refold upon relaxing of the magnetic force. In a ramp experiment, the nucleic acids are subjected to multiple cycles of slowly increasing and decreasing forces, and the forces at which the molecule unfolds or refolds can be determined from one or more sudden changes in Z bead position. In constant-force experiments, the nucleic acid is subjected to a constant force for a certain amount of time before increasing rapidly to a higher constant force, and so on in a step-wise manner. At one or more of these constant force levels, it is possible to observe the molecule transitioning between folded and unfolded states.

The method provided herein comprises exerting a force that is proportional to the energy required to modify the conformational structure of the nucleic acid in the presence of absence of at least one binding molecule.

In particular embodiments, the force is comprised between 0.1 to 100 piconewton, between 1 and 60 piconewton, between 1 to 35 piconewton, or between 1 to 40 or 45 piconewton. In some embodiments, the force is comprised between 1 to 45 piconewton. In some embodiments, the force is comprised between 1 to 40 piconewton. In some embodiments, the force is comprised between 1 to 35 piconewton.

In a ramp experiment, the nucleic acid (e.g., RNA) molecules are subjected to multiple cycles of slowly increasing and/or decreasing force, and the value at which the molecule unfolds or refolds can be determined from a sudden change in the bead's position. Upon binding, a ligand can cause a change in the unfolding or refolding force if it stabilizes or destabilizes the RNA structure.

In a Constant-Force Experiment, the nucleic acid molecules are subjected to the same force for a certain amount of time before it is increased in a stepwise manner. The equilibrium force is the point at which the molecule spends equal time in both folded and unfolded states. Ligand binding at this force can cause a change in the dynamics of folding and unfolding.

In some embodiments, the method described herein is carried out at a temperature comprised between 1° C. and 45° C., advantageously at a temperature comprised between 4° C. and 37° C., more advantageously at a temperature comprised between 15° C. and 25° C., even more advantageously at a temperature of 22° C.

Binding of a molecule (that can include amongst other things, molecules of low molecular weight, oligonucleotides, or polypeptides) to the target nucleic acid can affect the amount of force required to unfold or refold the nucleic acid structure. In some instances, binding of a binding molecule can stabilize the nucleic acid structure, and thereby increase the force required to unfold the nucleic acid structure. In some instances, binding of a binding molecule can destabilize or alter the nucleic acid structure, and thereby decrease the force required to unfold the nucleic acid structure. Molecules with a molecular weight of less than 1000 dalton are considered as small molecules. Molecules with a molecular weight of more than 1000 dalton but less than 10000 dalton may be also tested and considered as small molecules. The document Synthetic Small-Molecule RNA Ligands: Future Prospects as Therapeutic Agents. *MedChemComm*. Royal Society of Chemistry Aug. 14, 2019, pp 1242-1255 discloses an example of library comprising a plurality of small molecules. Once binding molecules are selected by the method described herein—or by another method allowing a molecule binding to a nucleic acid to be selected,—a library comprising analogs and/or chemically modified analogs of the selected members of the library of binding molecules initially selected, may be tested by the method disclosed herein.

By measuring the change in the unfolding and refolding forces at different concentrations of a binding molecule, the binding kinetics of candidate binding molecules can be determined. Further, a plurality of nucleic acid molecules can be screened at the same time at single molecule resolution. Such screening offers the ability to detect minimal differences in binding affinity, with increased resolution over other screening techniques. In particular embodiments, a plurality of molecules in a library means between 1 and $5\times10^6$ molecules or less than $1\times10^8$, for example between $1\times10^8$ and $1\times10^6$ molecules or for example 200000 molecules, or 4400 molecules, or even 750 molecules.

Accordingly, disclosed herein are methods for screening binding and non-binding molecules to a nucleic acid molecule, the method comprising: (a) attaching the plurality of nucleic acid molecules to a plurality of beads via a first end of the nucleic acid molecule; (b) attaching a plurality of nucleic acid molecules to a plurality of features of a device via a second end of the nucleic acid molecule; (c) contacting a chamber with a library of binding molecules, wherein each member of the library of binding molecules are contacted with a single nucleic acid molecule; (d) approaching a magnet to cause the plurality of beads to move relative to the bottom along an axis of the chamber and measuring a change in bead position via a sensor of the device based on movement of the bead relative to the bottom surface; (e) determining the unfolding forces of the nucleic acid molecule in the presence of each member of the library of binding molecules; (f) selecting members of the library of binding molecules that produce an unfolding force(s) of the nucleic acid molecule that is greater or smaller than an unfolding force of the nucleic acid molecule in the absence of the binding molecule; and (g) modeling the selected members of the library of binding molecules to identify a chemical signature of optimal binders among the library of binding molecules.

Systems

Provided herein are systems independently comprising one or more components of nucleic acids, DNA handles, beads, and at least one binding molecule. In some embodiments, the system comprises a library of the binding molecules. In some embodiments, the system further comprises a device (e.g., chamber) comprising a feature, wherein the feature is capable of being used for immobilizing the nucleic acid. In some embodiments, the device is capable of exerting a magnetic force to the bead. In some embodiments, the feature is operatively linked to a sensor that is capable of measuring impedance from the features caused by the movement of the beads up and down.

Nucleic Acid

Disclosed herein is a nucleic acid (or a target nucleic acid) that is immobilized on to a feature of a device and a bead. In some embodiments, the nucleic acid molecule (or a target nucleic acid) confers at least a potential secondary structure. In some embodiments, the secondary structure may be triggered upon binding of a molecule.

In some embodiments, a nucleic acid (or a target nucleic acid) comprises at least one conformational structure. A conformational structure of a nucleic acid (or a target nucleic acid) means a secondary or tertiary conformation, such as, for example, at least one of the conformations selected from a RNA hairpin, a P-shape RNA, a Y shape RNA, a candy shape RNA, and a combination thereof. Accordingly, in some embodiments, the nucleic acid comprises at least one secondary structure. In some embodiments, the nucleic acid comprises at least one hairpin structure.

In particular aspects, the nucleic acid can comprise an aptamer, in particular a DNA aptamer, a RNA aptamer, a XNA aptamer, or a combination thereof. In particular embodiments, the nucleic acid comprises an aptamer specific for a spike 1 protein of SARS-Cov- virus, a RNA aptamer specific for the spike 1 protein of SARS-Cov-2 virus, a XNA aptamer specific for the spike 1 protein of SARS-Cov-2 virus, or a peptide aptamer specific for the spike 1 protein of SARS-Cov-2 virus, or a combination thereof.

In some embodiments, a length of the nucleic acid is comprised between 10 bases and 1500 bases. In some embodiments, the length of the nucleic acid is between 15 bases and 2000 bases. In some embodiments, the length of the nucleic acid molecule is from about 20 bases to about 350 bases. In some embodiments, the length of the nucleic acid is less than 120 bases. In some embodiments, the length of the nucleic acid is more than 120 bases.

In some embodiments, a length of the nucleic acid is comprised between 10 bp and 1500 bp. In some embodiments, the length of the nucleic acid is between 15 bp and 2000 bp. In some embodiments, the length of the nucleic acid molecule is from about 20 bp to about 350 bp. In some embodiments, the length of the nucleic acid is less than 120 bp. In some embodiments, the length of the nucleic acid is more than 120 bp.

In some embodiments, the nucleic acid molecule is chemically synthesized. In some embodiments, the nucleic acid molecule is produced via in vitro transcription. In some embodiments, the nucleic acid molecule is produced via a polymerase chain reaction. In some embodiments, the nucleic acid molecule(s) is (are) purified from a cell.

In some embodiments, the nucleic acid described herein is capable of being immobilized onto the bead or the feature of the device by a covalent binding. In some embodiments, the nucleic acid is chemically linked to the bead or the feature of the device. In some embodiments, the nucleic acid is conjugated with a molecule comprising a first reactive group. In some embodiments, the first reactive group is capable of undergoing a chemical reaction with the second reactive group of the bead or the feature of the device described herein and form a covalent bond. In some embodiments, the chemical reaction occurs between two reactive groups comprising: (a) DBCO group and azide group; (b) tosyl group and amino group; (c) tosyl group and sulfhydryl group; (d) epoxy group and thiol group; (e) epoxy group and amino group; (f) epoxy group and hydroxyl group; or (g) chloromethyl group and amino group.

Alternatively, in some embodiments, the nucleic acid described herein is capable of being immobilized onto the bead or the feature of the device by a covalent binding. In some embodiments, the nucleic is non-covalently linked (e.g., biotin-streptavidin interaction) to the bead of the feature of the device. In some embodiments, the nucleic acid is conjugated to a biotin moiety. In some embodiments, the nucleic acid is conjugated to the biotin moiety at one or both ends of the nucleic acid.

In some embodiments, the nucleic acid described herein comprises a nucleic acid of interest. In some embodiments, the nucleic acid further comprises an orienting sequence linked to one or both ends of the nucleic acid of interest. In some embodiments, the orienting sequence is capable of being hybridized to the DNA handle described herein. Accordingly, in some embodiments, the orienting sequence comprises a nucleotide sequence that is complementary to the DNA handle. In some embodiments, the orienting sequence comprises at least 5 bases, at least 10 bases, at least 15 bases, at least 20 bases, at least 25 bases, at least 30 bases, at least 35 bases, at least 40 bases, at least 45 bases, at least 50 bases or more. In some embodiments, the nucleic acid described herein is capable of being immobilized onto the bead or the feature of the device by hybridizing to the DNA handle, wherein the DNA handle is linked to the bead or the feature of the device. In some embodiments, the orienting sequence forms a sticky end for the nucleic acid. Accordingly, in some embodiments, the nucleic acid comprising the DNA of interest, as described herein, comprises two strands that are at least partially not complementary to each other.

In some embodiments, the nucleic acid of interest described herein is involved in or responsible for the etiology of a disease. In some embodiments, the nucleic acid is involved in preventing or treating a disease. As a control or as a comparative, the same nucleic acid devoid of epigenetic markers or lacking a mutation responsible for a disease, or combined to its complementary RNA or DNA sequence, may be used.

In some embodiments, the nucleic acid of interest described herein is a viral nucleic acid molecule, the nucleic acid of interest is isolated from a bacteria, preferably isolated from a pathogenic viral agent or from a pathogenic bacterial agent. In some embodiments, the nucleic acid of interest is from a cell isolated from a cancer, from a pathological tissue, such as, a tumor or an amyloid plaque. In some embodiments, the nucleic acid of interest is a viral RNA isolated from a RNA virus, more preferably a viral RNA from a corona virus, even more preferably a viral RNA from a SARS or MERS virus, or SARS-COV-2 virus. In some embodiments, the nucleic acid of interest is isolated from an HIV-1 isolat, is HV-1 TAR. In some embodiments, the nucleic acid of interest is preQ1 riboswitch. In some embodiments, the preQ1 riboswitch comprises a mutation, relative to a wild type preQ1 riboswitch, that is selected from the group consisting of: C15U, U7C, A10G, and U6C. In some embodiments, the nucleic acid of interest is pre-miR-21. In some embodiments, the nucleic acid of interest is DM1.

In some embodiments, a nucleic acid (or a target nucleic acid) comprises a nucleic acid of interest, linker(s), and orienting sequence(s). In some embodiments, the nucleic acid molecule comprises a construction comprising a nucleic acid of interest, a linker at the 5' and a linker at the 3' end of said nucleic acid, and two different orienting sequences. An example of linker and of orienting sequence is illustrated FIGS. 1B and 1C. In some embodiments, the nucleic acid of interest comprises a DNA, a RNA, a XNA, an aptamer, or a combination thereof or a plurality of nucleic acids, bound to at least one binding molecule of a library of binding molecules.

Figure 1B:
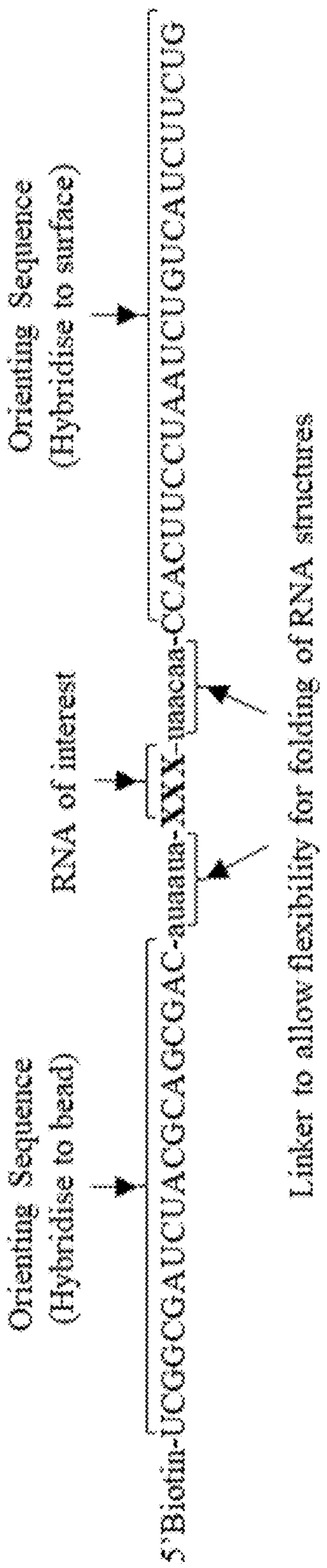
FIG. 1B shows exemplary structure of nucleic acid comprising target RNA (XXX) that can be used for analyzing the effect of small chemical compound binding according to an embodiment described herein. As shown, a sequence of the target RNA, known to form an RNA secondary structure, is inserted between two defined sequences on either side of XXX. The two defined sequences are engineered to generate handles to bind and orient the RNA molecule on the bead and the surface of the device.
Figure 1C:
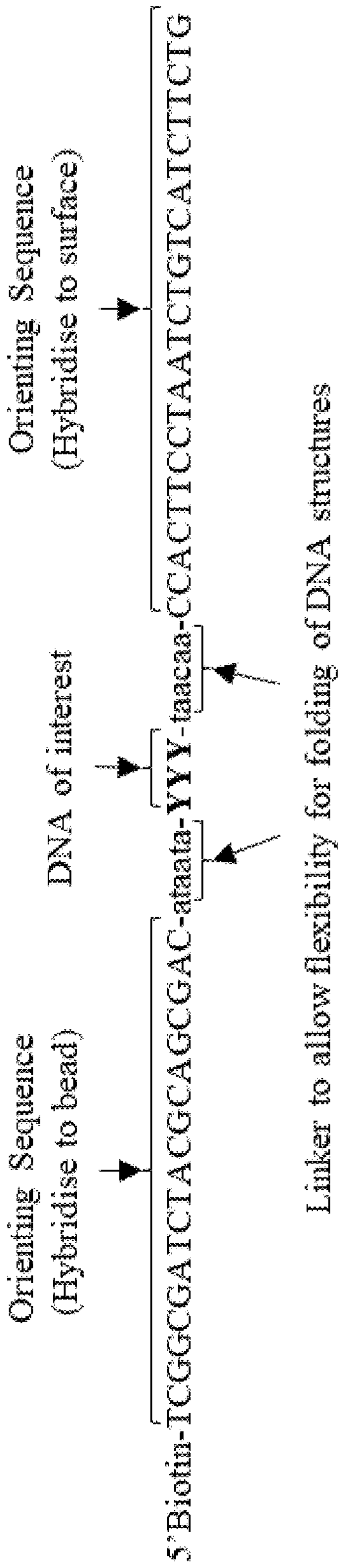
FIG. 1C shows exemplary structure of nucleic acid comprising a DNA molecule used to analyze the effect of small chemical compound binding. The sequence of the DNA (YYY) of interest, known to form a DNA secondary structure, is inserted between two defined sequences on either side. These sequences are used to generate handles to bind/orient the DNA molecule on the bead and the surface. These sequences are used as examples and can be changed.

In some embodiments, the nucleic acid of interest is a DNA or a RNA, as illustrated in FIGS. 1B and 1C, as (XXX)n and (YYY)n, respectively, wherein X may be ATG or C or Y may be AUG or C is a base, n=3 to n=1000, n=5 to n=500, X and Y may have an epigenetic marker such as a methyl.

In some embodiments, the nucleic acid molecule(s) of interest is an aptamer. Accordingly, in some embodiments, the nucleic acid of interest comprises a sequence comprising (XXX)n or (YYY)n, wherein X or Y is a base, n=3 to n=1000, n=5 to n=500, exemplified in FIGS. 1B and 1C. (XXX)n or (YYY)n can comprise (can consist of) an aptamer.

Table 1 illustrates exemplary nucleotide sequences of nucleic acids of interest that can be used to analyze the binding of small chemical molecules on secondary structures.

TABLE 1

| Exemplary Nucleic Acids of Interest | | |
|---|---|---|
| Structure | SEQ ID NO: | Sequence 5'-3' (RNA) |
| HIV-TAR | 1 | GGCUCUGGUUAGACCAGAUCUGAGCCUGGGAGCUCUCUGGCUAACUAGGGCC |
| Pre-miR-21 | 2 | UAGCUUAUCAGACUGAUGUUGACUGUUGAAUCUCAUGGCAACACCAGUCGAUGGGCUGU |
| preQ1 | 3 | AGAGGUUCUAGCUACACCCUCUAUAAAAAACUAA |
| Aptamer SARS-COV2 | 4 | GGCGACAUUUGUAAUUCCUGGACCGAUACUUCCGUCAGGACAGAGGUUGCCA |
| Aptamer MCP-1 | 5 | GGGAGGACGAUGCGGGAACUCACCGGGAAGAAGCCCGUUCCGUCACAGACAUGUUCCGCAUCGUCCUCCC |

In some embodiments, the nucleic acid described herein comprises any one of the nucleotide sequences recited in Table 1. In some embodiments, the nucleic acid sequence described herein comprises at least 10, at least 12, at least 14, at least 16, at least 18 or at least 20 consecutive nucleotides of any one of the sequences recited in Table 1. In some embodiments, any one of the nucleic acids of Table 1 is conjugated to biotin at 5' end or 3' end. Alternatives, in some embodiments, any one of the nucleic acids of Table 1 is conjugated to a molecule comprising dibenzocyclooctyne (DBCO) group at 5' end or 3' end. In some embodiments, any one of the nucleic acids of Table 1 is conjugated with biotin at one end and a molecule comprising dibenzocyclooctyne (DBCO) group at the other end.

In some embodiments, the one or both orienting sequences are linked to the nucleic acid of interest by a linker. Alternatively, in some embodiments, the nucleic acid does not comprise one or both orienting sequences. In such embodiments, the nucleic acid of interest comprises linker at one or both ends of the nucleic acid of interest. Table 2 provides exemplary linker sequences. In some embodiments, the linker comprises at least 1 base, at least 2 bases, at least 3 bases, at least 4 bases, at least 5 bases, at least 6 bases, at least 7 bases, at least 8 bases, at least 9 bases, at least 10 bases, at least 15 bases, at least 20 bases or more. In some embodiments, the linker comprises at least 1 bp, at least 2 bp, at least 3 bp, at least 4 bp, at least 5 bp, at least 6 bp, at least 7 bp, at least 8 bp, at least 9 bp, at least 10 bp, at least 15 bp, at least 20 bp or more.

TABLE 2

| Exemplary Linker Nucleotide Sequences | | |
|---|---|---|
| Seq ID No. | Type of Sequence | Nucleotide Sequence |
| 6 | RNA sequence | auauau |
| 7 | RNA sequence | uaacaa |
| 8 | RNA sequence | auaaua |
| 9 | RNA sequence | auau |
| 10 | RNA sequence | uaac |
| 11 | DNA sequence | ttgtta |
| 12 | DNA sequence | atatat |
| 13 | DNA sequence | aaaccc |
| 14 | DNA sequence | ataata |
| 15 | DNA sequence | taacaa |

The sequence of the nucleic acid of interest (XXX)n or (YYY)n, known to form at least one secondary structure, is inserted between two defined sequences (orienting sequences) flanking the object [linker-XXX-linker] or [linker-YYY-linker] (see FIG. 1B and FIG. 1C.) using linkers on either side of XXX or of YYY. The defined sequences allow to orient the nucleic acid of interest XXX or YYY and may be a single strand DNA, single strand RNA, etc. the 5' part of the XXX or YYY being linked to a biotin residue, for example. Table 3 provides exemplary nucleic acids as described in FIGS. 1B and 1C.

TABLE 3

| Exemplary Nucleotide Sequences | | |
|---|---|---|
| Seq ID No. | Seq. Type | Nucleotide Sequence (5' to 3') |
| 16 | RNA sequence | **UCGGCGAUCUACGCAGCGAC**auauauGGCGACAUUUGUAAUUCCUGGACCGAUACUUCCGUCAGGACAGAGGUUGCCAuaacaa**CACUCUCCUCAUCUGUCUCUCC** |
| 17 | RNA sequence | **UCGGCGAUCUACGCAGCGAC**auauGGGAGGACGAUGCGGGAACUCACCGGGAAGAAGCCCGUUCCGUCACAGACAUGUUCCGCAUCGUCCUCCCuaac**CACUCUCCUCAUCUGUCUCUCC** |
| 18 | RNA sequence | **UCGGCGAUCUACGCAGCGAC**auauauGGCUCUGGUUAGACCAGAUCUGAGCCUGGGAGCUCUCUGGCUAACUAGGGCCuaacaa**CCACUUCCUAAUCUGUCAUCUUCUG** |
| 19 | RNA sequence | **UCGGCGAUCUACGCAGCGAC**auauauAGAGGUUCUAGCUACACCCUCUAUAAAAAACUAAuaacaa**CCACUUCCUAAUCUGUCAUCUUCUG** |
| 20 | RNA sequence | **UCGGCGAUCUACGCAGCGAC**auauauUAGCUUAUCAGACUGAUGUUGACUGUUGAAUCUCAUGGCAACACCAGUCGAUGGGCUGUuaacaa**CCACUUCCUAAUCUGUCAUCUUCUG** |

TABLE 3-continued

Exemplary Nucleotide Sequences

| Seq ID No. | Seq. Type | Nucleotide Sequence (5' to 3') |
|---|---|---|
| 21 | RNA sequence | **UCGGCGAUCUACGCAGCGAC**auauauCUGCUGCUGCUGCUGCUGCUGCUGCUGCUGCUGCUGCUGCUGCUGCUGCUGCUGCUGCUGuaacaa**CCACUUCCUAAUCUGUCAUCUUCUG** |
| 22 | RNA sequence | **UCGGCGAUCUACGCAGCGAC**auauauUUGUAUAACCUCAAUAAUAUGGUUUGAGGGUGUCUACCAGGAACCGUAAAAUCCUGAUUACAAuaacaa**CCACUUCCUAAUCUGUCAUCUUCUG** |
| 23 | RNA sequence | **UCGGCGAUCUACGCAGCGAC**auauauUUAGACCAGAUCUGAGCCUGGGAGCUCUCUGGCUAAuaacaa**CCACUUCCUAAUCUGUCAUCUUCUG** |
| 24 | RNA sequence | **UCGGCGAUCUACGCAGCGAC**auaauaCUGGGUCGCAGUAACCCCAGUUAACAAAACAAGuaacaa**CCACUUCCUAAUCUGUCAUCUUCUG** |
| 25 | RNA sequence | **UCGGCGAUCUACGCAGCGAC**auaauaAGAGGCUCUAGCUACACCCUCUAUAAAAAACUAAuaacaa**CCACUUCCUAAUCUGUCAUCUUCUG** |
| 26 | RNA sequence | **UCGGCGAUCUACGCAGCGAC**auaauaAGAGGUUCUGGCUACACCCUCUAUAAAAAACUAAuaacaa**CCACUUCCUAAUCUGUCAUCUUCUG** |
| 27 | RNA sequence | **UCGGCGAUCUACGCAGCGAC**auaauaAGAGGUUCUAGCUAUACCCUCUAUAAAAAACUAAuaacaa**CCACUUCCUAAUCUGUCAUCUUCUG** |
| 28 | RNA sequence | **UCGGCGAUCUACGCAGCGAC**auaauaAGAGGUCCUAGCUAUACCCUCUAUAAAAAACUAAuaacaa**CCACUUCCUAAUCUGUCAUCUUCUG** |
| 29 | RNA sequence | **UCGGCGAUCUACGCAGCGAC**auauauUAGCUUAUCAGACUGAUGUUGACUGUUGAAUCUCAAUGGUCAACACCAGUCGAUGGGCUGUuaacaa**CCACUUCCUAAUCUGUCAUCUUCUG** |
| 30 | RNA sequence | **UCGGCGAUCUACGCAGCGAC**auauauCUGCUGCUGCUGCUGCUGCUGCUGCUGCUGCUGuaacaa**CCACUUCCUAAUCUGUCAUCUUCUG** |
| 31 | DNA sequence | **CAGAAGATGACAGATTAGGAAGTGG**ttgttaGGCCCTAGTTAGCCAGAGAGCTCCCAGGCTCAGATCTGGTCTAACCAGAGCCatatat**GTCGCTGCGTAGATCGCCGAGAATCTATAGTGAGTCGTATTA** |
| 32 | DNA sequence | **CAGAAGATGACAGATTAGGAAGTGG**ttgttaACAGCCCATCGACTGGTGTTGCCATGAGATTCAACAGTCAACATCAGTCTGATAAGCTAatatat**GTCGCTGCGTAGATCGCCGAGAATCTATAGTGAGTCGTATTA** |
| 33 | DNA sequence | **CAGAAGATGACAGATTAGGAAGTGG**ttgttaCAGCAGCAGCAGCAGCAGCAGCAGCAGCAGCAGCAGatatat**GTCGCTGCGTAGATCGCCGAGAATCTATAGTGAGTCGTATTA** |
| 34 | DNA sequence | **CAGAAGATGACAGATTAGGAAGTGG**ttgttaCAGCAGCAGCAGCAGCAGCAGCAGCAGCAGCAGCAGCAGCAGCAGCAGCAGCAGCAGCAGCAGatatat**GTCGCTGCGTAGATCGCCGAGAATCTATAGTGAGTCGTATTA** |
| 35 | DNA sequence | **CAGAAGATGACAGATTAGGAAGTGG**ttgttaGGCTAATGAATTCCTTTACACCACACTGTCGTCGAATGGCCACTCCCAGTatatat**GTCGCTGCGTAGATCGCCGAGAATCTATAGTGAGTCGTATTA** |
| 36 | DNA sequence | **CAGAAGATGACAGATTAGGAAGTGG**ttgttaAAGCCCTGTAGACGACATCAGTACTAGTGCCTGTGCCGCACGGTGTAAGACGGGCTGCACTTACACCGCaaaccc**GTCGCTGCGTAGATCGCCGAGAATCTATAGTGAGTCGTATTA** |
| 37 | DNA sequence | **CAGAAGATGACAGATTAGGAAGTGG**ttgttaAAGCCCTGTATACGACATCAGTACTAGTGCCTGTGCCGCACGGTGTAAGACGGGCTGCACTTACACCGCaaaccc**GTCGCTGCGTAGATCGCCGAGAATCTATAGTGAGTCGTATTA** |
| 38 | DNA sequence | **CAGAAGATGACAGATTAGGAAGTGG**ttgttaTTAGTTTTTATAGAGGGTGTAGCTAGAACCTCTatatat**GTCGCTGCGTAGATCGCCGAGAATCTATAGTGAGTCGTATTA** |
| 39 | DNA sequence | **CAGAAGATGACAGATTAGGAAGTGG**ttgttaCTTGTTTTGTTAACTGGGGTTACTGCGACCCAGatatat**GTCGCTGCGTAGATCGCCGAGAATCTATAGTGAGTCGTATTA** |

TABLE 3-continued

| Exemplary Nucleotide Sequences | | |
|---|---|---|
| Seq ID No. | Seq. Type | Nucleotide Sequence (5' to 3') |
| 40 | DNA sequence | **CAGAAGATGACAGATTAGGAAGTGG**ttgttaTTGTAATCAGGATTTTACGGTTCCTGGTAGACACCCTCAAACCATATTATTGAGGTTATACAAatatat**GTCGCTGCGTAGATCGCCGAGAATCTATAGTGAGTCGTATTA** |

*Bold uppercase represents orienting sequence, lowercase represents linker, uppercase represents nucleic acid of interest.

In some embodiments, the nucleic acid described herein comprises any one of the nucleotide sequences recited in Table 3. In some embodiments, any one of the nucleic acids of Table 3 is conjugated to biotin at 5' end or 3' end. In some embodiments, the nucleic acid described herein comprises any one of the RNA sequences of Table 3 that is conjugated to biotin at 5' end. Alternatives, in some embodiments, any one of the nucleic acids of Table 3 is conjugated to a molecule comprising dibenzocyclooctyne (DBCO) group, azide group, tosyl group, epoxy group, chloromethyl group, amino group, thiol group or hydroxyl group at 5' end or 3' end. In some embodiments, any one of the nucleic acids of Table 4 is conjugated with biotin at one end and a molecule comprising dibenzocyclooctyne (DBCO) group at the other end.

Accordingly, the invention provides the following object: A [magnetic bead-linker—streptavidine-biotin-orienting sequence linker-(XXX or YYY)n-linker—orienting sequence—feature with n is between 5 and $5\times10^2$ that is to say between 15 b and 1.5 kb, with X being a base constituent of a DNA, a natural or modified base constituent of a DNA, and Y being a base constituent of a RNA, a natural or modified base constituent of a RNA.

DNA Handle

DNA handle can be used to immobilize the nucleic acid (e.g., DNA, RNA, or a combination thereof) to a surface of a device and a bead. In some embodiments, a nucleic is immobilized onto a surface of the device by a DNA handle, wherein an orienting sequence of the nucleic acid is hybridized to at least a portion of the DNA handle. In some embodiments, the DNA handle is 90%, 95%, 96%, 97%, 98%, 99% or 100% complementary to the orienting sequence. In some embodiments, the DNA handle comprises at least 5 bases, at least 10 bases, at least 15 bases, at least 20 bases, at least 25 bases, at least 30 bases, at least 35 bases, at least 40 bases, at least 45 bases, at least 50 bases or more. In some embodiments, the DNA handle is chemically linked to the surface of the device. In some embodiments, the DNA handle is covalently linked to the surface of the device. In some embodiments, the DNA handle is conjugated with a molecule comprising a first reactive group that is capable of undergoing a chemical reaction with a second reactive group of the surface of the device to form a covalent bond. In some embodiments, the chemical reaction occurs between two reactive groups comprising: (a) DBCO group and azide group; (b) tosyl group and amino group; (c) tosyl group and sulfhydryl group; (d) epoxy group and thiol group; (e) epoxy group and amino group; (f) epoxy group and hydroxyl group; or (g) chloromethyl group and amino group. Accordingly, in some embodiments, the DNA handle comprises DBCO group and the surface of the device comprises azide group. Conversely, in some embodiments, the DNA handle comprises azide group and the surface of the device comprises DBCO group. In some embodiments, the DNA handle is non-covalently linked to the surface of the device. In such embodiments, the DNA handle is conjugated with a biotin moiety and the surface of the device comprises a streptavidin moiety, wherein the streptavidin moiety of the surface of the device is non-covalently bound with the biotin moiety of the DNA handle.

In some embodiments, a nucleic acid is immobilized onto a surface of a device, wherein a terminal nucleotide sequence of the nucleic acid is chemically linked to the surface of the device. In some embodiments, the terminal nucleotide sequence of the nucleic acid is covalently linked to the surface of the device. In some embodiments, the nucleic acid is conjugated with a molecule comprising a first reactive group that is capable of undergoing a chemical reaction with a second reactive group of the surface of the device to form a covalent bond. In some embodiments, the chemical reaction occurs between two reactive groups comprising: (a) DBCO group and azide group; (b) tosyl group and amino group; (c) tosyl group and sulfhydryl group; (d) epoxy group and thiol group; (e) epoxy group and amino group; (f) epoxy group and hydroxyl group; or (g) chloromethyl group and amino group. Alternatively, in some embodiments, the nucleic acid is immobilized onto the surface of the device, wherein: the nucleic acid is conjugated with a biotin moiety; the surface of the device comprises a streptavidin moiety; and the streptavidin moiety of the surface of the device is non-covalently bound to the biotin moiety of the nucleic acid.

In some embodiments, a nucleic acid is immobilized onto a bead, wherein the bead comprises a streptavidin moiety, and the nucleic acid is conjugated with a biotin moiety that is non-covalently bound with the streptavidin moiety of the bead. Alternatively, in some embodiments, the nucleic acid is chemically linked to the bead. Accordingly, in some embodiments, the nucleic acid is covalently linked to the bead. In some embodiments, the nucleic acid is conjugated to a molecule comprising a first reactive group that is capable of undergoing a chemical reaction to form a covalent bond with a second reactive group of the bead. In some embodiments, the chemical reaction occurs between two reactive groups comprising: (a) DBCO group and azide group; (b) tosyl group and amino group; (c) tosyl group and sulfhydryl group; (d) epoxy group and thiol group; (e) epoxy group and amino group; (f) epoxy group and hydroxyl group; or (g) chloromethyl group and amino group.

In some embodiments, a nucleic acid is immobilized onto a bead by a DNA handle, wherein a terminal nucleotide sequence of the nucleic acid is hybridized to at least a portion of the DNA handle. In some embodiments, the DNA handle is 90%, 95%, 96%, 97%, 98%, 99% or 100% complementary to the terminal nucleotide sequence. In some embodiments, the DNA handle is covalently linked to the bead. In some embodiments, the DNA handle is conjugated with a molecule comprising a first reactive group that is capable of undergoing a chemical reaction with a second reactive group of the bead to form a covalent bond. In some embodiments, the chemical reaction occurs between two reactive groups comprising: (a) DBCO group and azide group; (b) tosyl group and amino group; (c) tosyl group and sulfhydryl group; (d) epoxy group and thiol group; (e) epoxy group and amino group; (f) epoxy group and hydroxyl group; or (g) chloromethyl group and amino group. Alternatively, in some embodiments, the DNA handle is non-covalently linked to the bead. In such embodiments, the DNA handle is conjugated with a biotin moiety and the bead comprises a streptavidin moiety, wherein the streptavidin moiety of the bead is non-covalently bound with the biotin moiety of the DNA handle.

Table 4 provides exemplary nucleotide sequences of DNA handles that can be used for immobilizing a nucleic acid (e.g., DNA, RNA or a combination thereof).

TABLE 4

Exemplary DNA Handles

| Seq ID No. | Nucleotide Sequence (5' to 3') |
|---|---|
| 41 | CAGAAGATGACAGATTAGGAAGTGG |
| 42 | GTGTCTTTTGGTCTTTCTGGTGCTCTTCGAATCAGAAGATGACAGATTAGGAAGTGG |
| 43 | GTCGCTGCGTAGATCGCCGA |
| 44 | ATTCGAAGAGCACCAGAAAGACCAAAAGACAC |
| 45 | ATTCGAAGAGCACCAGAAAGACCAAAAGACACAGTCACAGAT |
| 46 | ATTCGAAGAGCACCAGAAAGACCAAAAGACACGACAGATCGCTCT |
| 47 | ATTCGAAGAGCACCAGAAAGACCAAAAGACACGACAGATCGCTCT/BCN-T/TGAGCGATCTGTC |
| 48 | GTGTCTTTTGGTCTTTCTGGTGCTCTTCGAAT |
| 49 | GGAGAGACAGATGAGGAGAGTG |
| 50 | GTGTCTTTTGGTCTTTCTGGTGCTCTTCGAATGGAGAGACAGATGAGGAGAGTG |
| 51 | TAATACGACTCACTATAG |
| 52 | TCGGCGATCTACGCAGCGAC |
| 53 | CCACTTCCTAATCTGTCATCTTCTG |

In some embodiments, the DNA handle described herein comprises any one of the nucleotide sequences recited in Table 4. In some embodiments, the DNA handle described herein comprises at least 10, at least 12, at least 14, at least 16, at least 18 or at least 20 consecutive nucleotides of any one of the sequences recited in Table 4. In some embodiments, any one of the DNA handles of Table 4 is conjugated to biotin at 5' end or 3' end. Alternatives, in some embodiments, any one of the DNA handles of Table 4 is conjugated to a molecule comprising dibenzocyclooctyne (DBCO) group at 5' end or 3' end. In some embodiments, one or more bases of the DNA handle sequences are modified chemically. In some embodiments, a modification to the DNA handle sequence comprises addition of an active primary amino group to one or more nucleotides. In some embodiments, the modification can be done by amino dT C6 reagent. Accordingly, in some embodiments, the modification is a BCN-I (bi cyclooctyne) modification. In some embodiments, the DNA handle comprising a modified nucleotide comprises a nucleotide sequence of SEQ ID NO: 47.

Bead

In some embodiments, the bead described herein is a magnetic bead. In some embodiments, the bead is linked to a DNA handle and/or a nucleic acid. In some embodiments, the magnetic bead comprises a non-conducting polymer, silicon, glass, or resin.

In some embodiments, the bead comprises a streptavidin moiety that is capable of bound to a biotin moiety of the DNA handle and/or the nucleic acid. Alternatively, in some embodiments, the bead comprises a first reactive group that is capable of undergoing a chemical reaction with a second reactive group of the DNA handle or the nucleic acid to form a covalent bond. In some embodiments, the chemical reaction occurs between two reactive groups comprising: (a) DBCO group and azide group; (b) tosyl group and amino group; (c) tosyl group and sulfhydryl group; (d) epoxy group and thiol group; (e) epoxy group and amino group; (f) epoxy group and hydroxyl group; or (g) chloromethyl group and amino group. Accordingly, in some embodiments, the bead comprises dibenzocyclooctyne (DBCO) group, azide group, tosyl group, epoxy group, chloromethyl group, amino group, thiol group or hydroxyl group.

In some embodiments, the magnetic bead comprises a diameter in a range of from 0.1 μm to 10 μm, from 0.3 μm to 10 μm, from 0.5 μm to 10 μm, from 1 μm to 10 μm, from 2 μm to 10 μm, from 5 μm to 10 μm, from 0.1 μm to 5 μm, from 0.3 μm to 5 μm, from 0.5 μm to 5 μm, from 1 μm to 5 μm, from 2 μm to 5 μm, from 0.1 μm to 2 μm, from 0.3 μm to 2 μm, from 0.5 μm to 2 μm, from 1 μm to 2 μm, from 0.1 μm to 1 μm, from 0.3 μm to 1 μm, from 0.5 μm to 1 μm, from 0.1 μm to 0.5 μm, from 0.3 μm to 0.5 μm or from 0.1 μm to 0.3 μm. In some embodiments, the magnetic bead comprises a diameter of 0.3 μm, 0.5 μm, 1.04 μm, 2.8 μm, or 5.5 μm.

Device

In some embodiments, the device described herein comprises an actuator, a sensor, and a chamber. In some embodiments, the actuator is adapted to cause the bead to move relative to the surface of the device in one direction of motion. In some embodiments, the sensor is adapted to measure a distance between the bead and the surface. In some embodiments, the chamber comprises an axis extending along the direction of motion of the bead and a bottom which is formed by a feature (e.g., surface).

In some embodiments, the bead described herein is a magnetic bead and a magnet is used to create a force that changes the position of the magnetic bead in the chamber. In some embodiments, a force of the magnet relative to the bead is constant. In some embodiments, a force of the magnet relative the bead is increased (ramp). Other devices are suitable such that those allowing to exert a force to unfold a nucleic acid whether or not a protein, an antibody, an aptamer is linked to the nucleic acid molecule. Changes in the position of the bead in the chamber are measured using the sensor of the device.

In some embodiments, a feature, as described herein, can represent at least 10,000 features. In some embodiments, the sensor comprises a camera, advantageously a CMOS camera, which is capable of collecting photons reflected from the beads. In some embodiments, the sensor comprises a CMOS capable of measuring impedance from the features caused by the movement of the beads up and down. In some embodiments, the nucleic acid molecule is a DNA molecule. In some embodiments, the nucleic acid molecule is an RNA molecule. In some embodiments, the nucleic acid molecule comprises a DNA/RNA hybrid molecule. In some embodiments, the plurality of nucleic acid molecules comprises the same nucleic acid molecule. In some embodiments, the plurality of nucleic acid molecules are different nucleic acid molecules. In some embodiment, the plurality of acid nucleic molecule differs from at least one or two bases from each other's.

Electrically Conductive Solution

In some embodiments, the system described herein comprises an electrically conductive solution disposed in the chamber described herein. In some embodiments, the chamber comprises a sensor that is adapted to measure an impedance of the chamber. In some embodiments, the impedance is a function of the distance between the bead and the feature (e.g., surface). In some embodiments, the electrically conductive solution can have a conductivity of between $10^{-7}$ S/cm and $10^{-1}$ S/cm, or between $10^{-3}$ and $10^{-2}$ S/cm.

Binding Molecule

In some embodiments, the system described herein comprises a binding molecule or a library of binding molecules. In some embodiments, the library of binding molecules comprising analogs and/or chemically modified analogs of the selected member(s) of the library of binding molecules. In some embodiments, the binding molecule is capable of binding to the nucleic acid described herein. In some embodiments, the binding molecule is capable of producing an unfolding force of the nucleic acid that is greater or less than an unfolding force of the nucleic acid in the absence of the binding molecule. In some embodiments, the unfolding force is dependent on an amount of the binding molecule.

In some embodiments, the library of binding molecules comprises an aptamer, in particular a DNA aptamer, a RNA aptamer, a XNA aptamer, a peptide aptamer, or a combination thereof. Aptamers, first described as artificial oligonucleotides that bind one or more specific target molecules, exhibit a range of affinities ($K_D$ in the pM to μM range), with little or no off-target binding. Aptamers may be considered as chemical antibodies.

Other examples of libraries of binding molecules can be found easily by the skilled person. The following libraries of binding molecules are examples of libraries of binding molecules suitable for the claimed method.

In some embodiments, the binding molecule described herein can stabilize a structure of the nucleic acid, and thereby increase the force required to unfold the structure of the nucleic acid. In some embodiments, the binding molecule described herein can destabilize or alter a structure of the nucleic acid, and thereby decrease the force required to unfold the structure of the nucleic acid. Molecules with a molecular weight of less than 1000 dalton are considered as small molecules. Molecules with a molecular weight of more than 1000 dalton but less than 10000 dalton may be also tested and considered as small molecules.

A binding molecule can include molecules that bind to the target nucleic acid (or nucleic acid) to an extent sufficient to affect the folding or unfolding force of the target nucleic acid. Such binding molecules can have a having a $K_D$ of about 0.01 nM, 0.02 nM, 0.03 nM, 0.04 nM, 0.05 nM, 0.06 nM, 0.07 nM, 0.08 nM, 0.09 nM, 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1 μM, 2 μM, 3 μM, 4 μM, 5 μM, 6 μM, 7 μM, 8 μM, 9 μM, 10 μM, 20 μM, 30 μM, 40 μM, 50 μM, 60 μM, 70 μM, 80 μM, 90 μM, 100 μM, 200 μM, 300 μM, 400 μM, 500 μM, 600 μM, 700 μM, 800 μM, 900 μM, 1 mM, 2 mM, 3 mM, 4 mM, 5 mM, 6 mM, 7 mM, 8 mM, 9 mM, 10 mM, 20 mM, 30 mM, 40 mM 50 mM, 60 mM, 70 mM, 80 mM, 90 mM, or 100 mM.

Binding molecules as disclosed herein can include small molecules, chemicals, polypeptides, or other polynucleotides as demonstrated in the examples. In a specific embodiment of the invention, binding molecules as disclosed herein can include polypeptides, or other polynucleotides as demonstrated in the examples. In some embodiments, the binding molecule is a medicament.

Methods of Identifying A Chemical Signature

Disclosed herein is a method of identifying a chemical signature of optimal binders among a library of binding molecules to a nucleic acid molecule is provided, said method comprises: (a) attaching a first terminal of a nucleic acid molecule to a bead; (b) attaching a second terminal of the nucleic acid molecule to a feature of a device in a chamber, said chamber comprising a bottom surface and an axis, said device further comprising a sensor for detecting a position of the bead; (c) optionally exerting a force onto the nucleic acid, to unfold said nucleic acid and let the nucleic acid refolding, as a control; (d) contacting the nucleic acid molecule with a library of molecules, wherein each member of the library of binding molecules are contacted with a single nucleic acid molecule; (e) exerting a force onto the nucleic acid to unfold said nucleic acid; (f) selecting members of the library of binding molecules that produce an unfolding force of the nucleic acid molecule that is greater or smaller than an unfolding force of the nucleic acid molecule in the absence of the binding molecules; (g) modeling the selected members of the library of binding molecules to identify a chemical signature of optimal binders among the library of binding molecules; and (g) optionally, testing the activity of the optimal binders or (g), and their analogs/chemically modified binders, as a medicament.

Also disclosed herein are methods of identifying a chemical signature of optimal binders among a library of binding molecules to a nucleic acid molecule; the method comprising: (a) attaching the plurality of nucleic acid molecules to a plurality of beads via a first end of the nucleic acid molecule; (b) attaching a plurality of nucleic acid molecules to a plurality of features of a device via a second end of the nucleic acid molecule; (c) contacting a chamber with a library of binding molecules, wherein each member of the library of binding molecules are contacted with a single nucleic acid molecule; (d) approaching a magnet to cause the plurality of beads to move relative to the bottom surface of the feature along an axis of the chamber and measuring a change in bead position via a sensor of the device based on movement of the bead relative to the bottom surface; (e) determining an unfolding force of the nucleic acid molecule in the presence of each member of the library of binding molecules; (f) selecting members of the library of binding molecules that produce an unfolding force of the nucleic acid molecule that is greater or less than an unfolding force of the nucleic acid molecule in the absence of the binding molecule; and (f) modeling the selected members of the library of binding molecules to identify a chemical signature of optimal binders among the library of binding molecules.

Methods and Systems for Determining Binding Kinetics

Disclosed herein are methods of determining binding kinetics of a binding molecule to a nucleic acid molecule comprising: (a) attaching an end of a nucleic acid molecule to a bead; (b) attaching an end of the nucleic acid molecule to a feature of a device in a chamber, said chamber comprising a bottom surface and an axis, said device further comprising a sensor for detecting a position of the bead; (c) contacting the nucleic acid molecule with increasing concentrations of a binding molecule; (d) exerting a force onto the nucleic acid, to unfold said nucleic acid; (e) determining an unfolding force of the nucleic acid molecule as a function of the concentration of the binding molecule; and (f) calculating the binding kinetics of the binding molecule to the nucleic acid molecule based on the change unfolding force as a function of the amount of the binding molecule.

Also disclosed herein are methods of determining binding kinetics of a binding molecule to a nucleic acid molecule, the method comprising: (a) attaching the plurality of nucleic acid molecules to a plurality of beads via a first end of the nucleic acid molecule; (b) attaching a plurality of nucleic acid molecules to a plurality of features of a device via a second end of the nucleic acid molecule; (c) contacting a chamber with increasing concentrations of the binding molecule; (d) applying a magnetic field sufficient to cause each bead of the plurality of beads to move relative to the bottom surface of the feature of the chamber and measuring a change in bead position via a sensor of the device based on movement of the bead relative to the bottom surface; (e) determining an unfolding force of the nucleic acid molecule as a function of the concentration of the binding molecule; and (f) calculating the binding kinetics of the binding molecule to the nucleic acid molecule based on the change unfolding force as a function of the amount of the binding molecule.

Also disclosed herein are systems for determining the binding kinetics of a binding molecule to a nucleic acid molecule. In some embodiments, the system comprises: (a) a plurality of the nucleic acid molecules attached to a plurality of beads via one end of the nucleic acid molecule; (b) a plurality of nucleic acid molecules attached to a plurality of features of a device via a second end of the nucleic acid molecule; (c) a chamber with a library of binding molecules, wherein increasing doses of each member of the library of binding molecules are contacted with a plurality of single nucleic acid molecule in a single chamber; (d) a magnet to cause the plurality of beads to move relative to a bottom surface along an axis of the chamber; and (e) a sensor to measure a change in bead position of the device based on movement of the bead relative to the bottom surface.

Methods of Screening

In some embodiments, a method of screening is provided comprising: (a) attaching a nucleic acid molecule with at least two ends to a magnetic bead at one end; (b) attaching another end of the nucleic acid molecule to a feature of a device comprising a sensor for detecting a change in the position of the magnetic bead; (c) exerting a force by approaching a magnet to the magnetic bead to change the magnetic bead position relative to the bottom surface, and unfold the nucleic acid; (d) optionally contacting said nucleic acid to at least one molecule, before or after refolding the nucleic acid; (e) quantifying the change in the magnetic bead position or unfolding force before and after contacting the nucleic acid molecule with a library of binding molecules; and (f) selecting binding molecule(s) that produce(s) an unfolding force of the nucleic acid molecule that is greater or smaller than an unfolding force of the nucleic acid molecule in the absence of the binding molecule. In some embodiments, the method further comprises repeating the step (a) to (d) with a library of binding molecules comprising analogs and/or chemically modified analogs of the selected member(s) of the library of binding molecules. In some embodiments, the method further comprises testing the activity of the selected binding molecule(s), and/or their analogs/modified versions, as a medicament.

Disclosed herein are methods of screening or identifying binding molecules to a nucleic acid molecule comprising: (a) orienting a nucleic acid molecule or a plurality of nucleic acid molecules with a 5' end and a 3' end in a device by attaching the 5' end to a bead and the 3' end to a bottom surface of a device, the device further comprising a sensor for detecting a position of the bead; (b) contacting the nucleic acid molecule with a library of molecules, before, during or after exerting a force onto the nucleic acid by approaching a magnet to the magnetic bead; and (c) measuring a change in the magnetic bead position via the sensor of the device based on a movement of the bead relative to the bottom surface.

In some embodiments, the method comprises: (a) measuring a conformational change of a nucleic acid by exerting a force onto the nucleic acid molecule before, during and after contact between the nucleic acid and a plurality of molecules and/or increasing doses of a molecule; and (b) selecting molecule(s) binding directly or indirectly to the nucleic acid. In some embodiments, the method further comprises, testing said molecule as a medicament for the prevention and/or the treatment of a disease linked to said nucleic acid.

In some embodiments, a conformational change of a nucleic acid linked to a magnetic bead is carried out in real time by exerting a force, advantageously a series of constant force or a series of increasing forces onto the nucleic acid molecule using a magnet and measuring a movement of a bead linked to the nucleic acid. This step is repeated before, after, or upon contact between the nucleic acid and a plurality of molecules and/or increasing doses of a molecule. Accordingly, in some embodiments, the nucleic acid described herein comprises at least one conformational structure alone or upon contact with a molecule.

In some embodiments, the method comprises: (a) attaching a 5' end of a nucleic acid molecule to a bead; (b) attaching a 3' end of the nucleic acid molecule to a feature of a device in a chamber, said chamber comprising a bottom surface and an axis, said device further comprising a means for detecting the binding of a molecule as a function of a conformation of the nucleic acid; (c) contacting a plurality of molecules from a library with the nucleic acid before or during exerting a force onto the nucleic acid; (d) identifying molecules that produce an unfolding force of the nucleic acid molecule that is greater or smaller than an unfolding force of the nucleic acid molecule in the absence of the binding molecules; and (e) testing analogs, chemically modified molecules. In some embodiments, the method further comprises testing the activity of the selected binding molecule(s) as a medicament. In some embodiments, the binding is determined by measuring the $K_d$, the $K_{on}$, and/or $K_{off}$ of a selected binding molecule.

Disclosed herein are methods for identifying binding molecules to a nucleic acid molecule comprising a first end and a second end, the method comprising: (a) attaching a plurality of nucleic acid molecules to a plurality of beads via a first end of the nucleic acid molecule; (b) attaching a plurality of nucleic acid molecules to a plurality of features of a device via a second end of the nucleic acid molecule; (c) contacting a chamber with a library of binding molecules, wherein each member of the library of binding molecules at increasing doses, is contacted with a single nucleic acid molecule; (d) approaching a magnet to cause the plurality of beads to move relative to the bottom along an axis of the chamber and measuring a change in bead position via a sensor of the device based on movement of the bead relative to the bottom surface, (e) determining the unfolding forces of the nucleic acid molecule in the presence of each member of the library of binding molecules; (f) differentiating between members of the library of binding molecules that produce an unfolding force(s) of the nucleic acid molecule that is greater or smaller than an unfolding force of the nucleic acid molecule in the absence of the binding molecule; and (g) modeling the selected members of the library of binding molecules to identify a chemical signature of optimal binders among the library of binding molecules. In some embodiments, the method further comprises testing the activity of the identified molecule(s) in preventing or treating a disease directly or indirectly linked to the bound or unbound RNA.

In some embodiments, the method comprises: (a) attaching a nucleic acid molecule comprising two ends to a bead via one end; (b) attaching a second end of the nucleic acid molecule to a feature of a device; (c) contacting a chamber with a library of binding molecules, wherein each member of the library of binding molecules is contacted with a plurality of single nucleic acid molecule in a single chamber; (d) approaching a magnet to cause the bead to move relative to a bottom surface along an axis of the chamber and measuring a change in bead position via a sensor of the device based on movement of the bead relative to the bottom surface; (e) determining an unfolding force of the nucleic acid molecule in the presence of each member of the library of binding molecules; and (f) selecting members of the library of binding molecules that produce an unfolding force of the nucleic acid molecule that is greater or smaller than an unfolding force of the nucleic acid molecule in the absence of the binding molecule. In some embodiments, the method further comprises testing the activity of the identified binding molecule, as a medicament to prevent or treat a disease directly or indirectly related to the nucleic acid.

In some embodiments, a disease directly related to the nucleic acid comprises a disease that is related to the exposure of a body or a cell, to the nucleic acid, or to an infectious agent comprising said nucleic acid.

In some embodiments, a disease indirectly related to the nucleic acid comprises a disease that is related to the exposure of a body or a cell to the nucleic acid and/or to a product derived from the nucleic acid by transcription, translation, replication, or a combination thereof.

The method provided herein can detect and/or identify molecule(s) that bind to a conformational structure of a nucleic acid or near this conformational structure. A nucleic acid can be a plurality of identical nucleic acids or a plurality of different nucleic acid molecules. A plurality of nucleic acids binds to a plurality of beads. In particular embodiments, the nucleic acid molecule comprises several motifs that can be recognized by an aptamer. In particular embodiments, the nucleic acid molecule can be an aptamer.

In some embodiments, the method further comprises a step of contacting the nucleic acid, said nucleic acid comprises (or is, or consists of) an aptamer, and analysing the binding of a small molecule, a protein such as an enzyme interacting with said nucleic acid. In some embodiments, the method further comprises a step of contacting the nucleic acid with a molecule x (before, during or after unfolding the nucleic acid in the presence or the absence of molecules from a library), said molecule x may be a protein, that may be Bovine Serum Albumine (BSA) to block the non-specific binding, an antibody, particularly, an antibody specific for an epigenetic marker, an antibody specific for a methyl or an acetyl, an enzyme interacting with said nucleic acid at one point of the translation, a cofactor. In some embodiments, the method further comprises a step of contacting the nucleic acid with a molecule x (before, during or after unfolding the nucleic acid in the presence or the absence of molecules from a library), said molecule x may be an aptamer. This optional step of contacting the nucleic acid with a molecule x may take place before during or after contact with the molecules of the library.

In the case of a plurality of identical nucleic acid, a chemical signature of optimal binders among a library of binding molecules, may be provided. Accordingly, also disclosed herein are methods of identifying a chemical signature of optimal binders among a library of binding molecules to a nucleic acid molecule, the method comprises: (a) contacting a single nucleic acid molecule with a library of binding molecules, wherein each member of the library of binding molecules is contacted with a single nucleic acid molecule; (b) approaching a magnet to cause the plurality of beads to move relative to a bottom surface along an axis of the chamber and measuring a change in bead position via a sensor of the device based on movement of the bead relative to the bottom surface, (c) determining an unfolding force of the nucleic acid molecule in the presence of each member of the library of binding molecules; (d) selecting members of the library of binding molecules that produce an unfolding force of the nucleic acid molecule that is greater or smaller than an unfolding force of the nucleic acid molecule in the absence of the binding molecule; and (e) modeling the selected members of the library of binding molecules to identify a chemical signature of optimal binders among the library of binding molecules.

As disclosed herein, a plurality of binding molecules can be screened for their ability to bind to a target nucleic acid molecule. In some instances, a plurality of the same target nucleic acid molecule can be immobilized for screening using the platform device described herein. In some instances, a plurality of different target nucleic acid molecules can be immobilized for screening using the platform device described herein. The unfolding and refolding force can be calculated using ramp force experiments as described in the examples below. The kinetics of the binding of a molecule (e.g., $K_{on}$ and $K_{off}$) can be calculated using constant force experiments as described in the examples below. The effect of ligand binding on the unfolding and refolding forces can be used to differentiate among molecules that bind to a target nucleic with varying binding affinities.

In some instances, multiple candidates can be screened for their ability to bind to a target nucleic acid. In some instances, tests can be completed on the same target molecule (as this is a single molecule platform) and the process can be non-destructive. For example, the chamber containing a single target nucleic acid can be screened with individual candidates, and their ability to bind to the target nucleic acid can be determined by the change in the unfolding and refolding forces upon contact with the candidates. Candidates that are able to bind to a target nucleic acid (i.e. those that have the greatest effect on the unfolding or refolding forces as measured by impedance) or using an optical device) can be rapidly identified. Further, the methods described herein can distinguish between binders having a dynamic range of binding affinities. For example, the methods described herein can identify binders having a $K_D$ of about 0.01 nM, 0.02 nM, 0.03 nM, 0.04 nM, 0.05 nM, 0.06 nM, 0.07 nM, 0.08 nM, 0.09 nM, 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1 μM, 2 μM, 3 μM, 4 μM, 5 μM, 6 μM, 7 μM, 8 μM, 9 μM, 10 μM, 20 μM, 30 μM, 40 μM, 50 μM, 60 μM, 70 μM, 80 μM, 90 μM, 100 μM, 200 300 μM, 400 μM, 500 μM, 600 μM, 700 μM, 800 μM, 900 μM, 1 mM, 2 mM, 3 mM, 4 mM, 5 mM, 6 mM, 7 mM, 8 mM, 9 mM, 10 mM, 20 mM, 30 mM, 40 mM 50 mM, 60 mM, 70 mM, 80 mM, 90 mM, or 100 mM. Further, the methods described herein can distinguish between binders having from less than 30 fold, less than 20 fold, less than 10-fold, less than 9-fold, less than 8-fold, less than 7-fold, less than 6-fold, less than 5-fold, less than 4-fold, less than 3-fold, less than 2-fold, less than 1-fold, less than 0.9-fold, less than 0.8-fold, less than 0.7-fold, less than 0.6-fold, less than 0.5-fold, less than 0.4-fold, less than 0.3-fold, less than 0.2-fold, or less than 0.1-fold difference in unfolding or refolding force. In some embodiments, the methods described herein can distinguish between binders having from about 0.1 fold to about 30-fold differences in unfolding or refolding force.

A target nucleic acid as described herein can include a target DNA, target RNA, or hybrid, implicated in a disease or condition. For example, a target nucleic acid can include HIV-1 TAR, preQ1 riboswitch, pre-miR-21, MYC, APOC3, DM1, C9orf72, MAPT, or FMR1. Alternatively and additionally, a target nucleic acid can include HIV-1 TAR, preQ1 riboswitch, pre-miR-21, MYC, APOC3, DM1, C9orf72, MAPT, or FMR1, an aptamer binding to SARS-Cov-2 spike.

Examples of such nucleic acids are in Table 3. A target nucleic acid can be chemically synthesized prior to immobilization, can be recombinantly produced in a microorganism, or can be produce by in vitro transcription. In some cases, a nucleic acid molecule can be produced via a polymerase chain reaction. Such target nucleic acids can range in size from about 10 bp to about 1000 bp, or from about 10 bp to 1500 bp (e.g., from about 20 to about 350 bp, from about 50 to about 200 bp, from about 75 to about 150 bp, etc.). In some embodiments, the target nucleic acids can range in size from about 10 to about 1000 bases, or from about 10 to 1500 bases (e.g., from about 20 to about 350 bases, from about 50 to about 200 bases, from about 75 to about 150 bases, etc.).

In some embodiments, a target nucleic acid can be a nucleic acid having native modifications. Indeed, nucleic acids having native modifications (post-transcriptional/epigenetic) may interact with a binding molecule differently than nucleic acids having no modification. Thus, the methods described herein can be used to distinguish between modified and unmodified nucleic acids. Such a method can be used to screen for modifications implicated in a disease or condition. Specifically, nucleic acid can be isolated from a subject suspected of having a disease or condition, which can be immobilized in a feature as described herein. Where the force of unfolding and refolding in the presence of a given ligand is known for a modified and an unmodified target, the presence or absence of a modification can be quickly determined by determining the unfolding and refolding forces of the nucleic acid isolated from the subject in the presence of ligand and comparing to the standards.

Kits

Also disclosed herein are systems for practicing the methods disclosed herein. In some cases, a kit can comprise a system disclosed herein. In some cases, an apparatus can comprise a system disclosed herein. For example, a system can comprise (a) a plurality of the nucleic acid molecules attached to a plurality of magnetic beads via one end of the nucleic acid molecule; (b) a plurality of nucleic acid molecules attached to a plurality of features of a device via a second end of the nucleic acid molecule, (c) a chamber with a library of binding molecules, wherein each member of the library of binding molecules are contacted with a plurality of single nucleic acid molecule in a single chamber; and (d) a magnet to cause the plurality of beads to move relative to a bottom surface of the feature along an axis of the chamber; and (e) a sensor to measure a change in bead position of the device based on movement of the bead relative to the bottom surface. In some cases, a system can be used for screening binding molecules to a nucleic acid molecule. In some cases, a system can be used for determining the binding kinetics of a binding molecule to a nucleic acid molecule. In some cases, a kit can comprise a container and instructions for use. Also, provided herein are kits comprising: (a) a nucleic acid molecule, or a plurality of the same or of different nucleic acid molecules comprising an orienting sequence at one end and a biotin moiety at the other end; (b) a DNA handle comprising a first reactive group, wherein the DNA handle is capable of hybridizing to the orienting sequence; (c) a feature of a device comprising a second reactive group that is capable of undergoing a chemical reaction with the first reactive group; and (d) a bead or a plurality of beads comprising streptavidin moiety that is capable of binding to the biotin moiety. Also provided herein are kits comprising: (a) a nucleic acid molecule, or a plurality of the same or of different nucleic acid molecules comprising a first orienting sequence at one end and a second orienting sequence at the other end; (b) a first DNA handle comprising a biotin moiety, wherein the first DNA handle is capable of hybridizing to the first orienting sequence; (b) a second DNA handle comprising a first reactive group, wherein the DNA handle is capable of hybridizing to the second orienting sequence; (c) a feature of a device comprising a second reactive group that is capable of undergoing a chemical reaction with the first reactive group; and (d) a bead or a plurality of beads comprising streptavidin moiety that is capable of binding to the biotin moiety. In some embodiments, the kit further comprises a library of binding molecules. In some embodiments, the library of binding molecules comprises a library of small molecules, a library of proteins, a library of antibodies, a library of aptamers, advantageously a library comprising binding molecules. In some embodiments, the kit further comprises a buffer comprising a divalent cation in a range of from 1 μM to 1 mM. In some embodiments, the divalent cation comprises $Mg^{2+}$, $Mn^{2+}$, $Zn^{2+}$, $Fe^{2+}$, $Cu^{2+}$, or $Cd^{2+}$. In some embodiments, the chemical reaction is an esterification reaction. In some embodiments, the chemical reaction is a click chemistry.

As another aspect, provided herein is a kit (or a system) comprising: (a) a nucleic acid molecule, or a plurality of the same or of different nucleic acid molecules, covalently linked, at one end, to a bead using a linker, a DNA handle, and/or a click, advantageously using a biotin and a streptavidin moiety; (b) the nucleic acid is attached, at another end, to a feature at a bottom surface of a chamber, in a device; (c) attachment at another end, to a feature at a bottom surface of a chamber, may be performed using a linker, a DNA handle, and/or a click; (d) said device further comprises a sensor for detecting a position of the bead; a magnet; (e) a library of binding molecules, such as a library of small molecules, a library of proteins, a library of antibodies, a library of aptamers; and (f) a buffer, advantageously a buffer comprising a divalent cation, such as $Mg^{2+}$, $Mn^{2+}$, $Zn^{2+}$, $Fe^{2+}$, $Cu^{2+}$, $Cd^{2+}$, preferably $Mg^{2+}$. In some embodiments, the buffer contains less than 10 mM $Mg^{2+}$, less than 5 mM $Mg^{2+}$, advantageously >0.01 mM $Mg^{2+}$ and less than 10 mM $Mg^{2+}$, more advantageously 1 mM $Mg^{2+}$.

In some embodiments, provided herein is a kit comprising: (a) a nucleic acid molecule, or a plurality of nucleic acids; (b) a bead or a plurality of beads; (c) at least two linkers, a DNA handle and/or a click; and (d) two orienting sequences. In some embodiments, the bead is a magnetic bead.

In some embodiments, provided herein is a device comprising: a feature at a bottom surface of a chamber, said device further comprising a sensor, advantageously a magnetic sensor; at least one library of binding molecules; and a buffer.

Platform

A method of screening as described herein can utilize a device for measuring unfolding and refolding of a target nucleic acid. A device can include a device described in U.S. Pat. No. 10,933,416, which is incorporated by reference in its entirety. One of the devices and/or one part of the devices that may be used to achieve such an unfolding of the nucleic acid and detect it, is disclosed for example in patent WO2016177869. Thus, an optical device that can detect the unfolding of the sampled nucleic acid may be those described in EP3181703B or in EP3990958, technical EP3505641, preferably in, or in EP3914949, EP3803492; all entirely included by reference.

Other embodiments of the device as described herein can also include: (a) a magnetic bead (e.g. a magnetic bead "MyOne", produced by Invitrogen, having a diameter of 1.04 μm; M270, produced by Invitrogen, of 2.8 μm diameter; M450, produced by Invitrogen, of 5.5 μm diameter; Ademtech 500, produced by Ademtech, of 0.5 μm diameter; Ademtech 300, produced by Ademtech, of 0.3 μm diameter) on which one end of a target nucleic acid can be attached; (b) a surface (e.g. silicon, glass, a non-conducting polymer or resin), on which a second end of the target nucleic acid can be attached; (c) an actuator, adapted to cause the bead to move relative to the surface of the device in one direction of motion; (d) a sensor, adapted to measure a distance between the bead and the surface; (e) a chamber, having an axis extending along the direction of motion of the bead and a bottom which is formed by the surface; and (f) an electrically conductive solution disposed in the chamber, where the electrically conductive solution can have a conductivity of between $10^{-7}$ S/cm and $10^{-1}$ S/cm, or between $10^{-3}$ and $10^{-2}$ S/cm, where the sensor is adapted to measure an impedance of the chamber, where the impedance is a function of the distance between the bead and the surface.

Also disclosed herein are systems or devices (platforms) for selecting a molecule(s) binding to a conformational state of a nucleic acid in real time comprising a plurality of magnetic beads, a magnet, a feature in a chamber, and a sensor for detecting the movement of a bead linked to a nucleic acid as a function of a change in confirmation of the nucleic acid. In some embodiments, the chamber comprises a bottom surface and an axis.

In some embodiments, a device can include a device described in U.S. Pat. No. 9,933,609, which is incorporated by reference in its entirety. In some embodiments, a device can include a device described in U.S. Pat. No. 10,209,505, which is incorporated by reference in its entirety. A device as described herein can include: a) an objective for collecting light radiations diffused by an object, the imaging system having an optical axis extending parallel to the first axis; b) a transmission mask having at least a first aperture and a second aperture, the first aperture and second aperture being spaced from each other along a second axis, perpendicular to the first axis, the transmission mask being arranged so as to let a first part of the radiations and a second part of the radiations which are diffused by the object pass through the first aperture and the second aperture respectively, while blocking a part of the radiations emitted by the light source which is not diffused by the object; and c) a detector adapted for generating an image including a first spot and a second spot representative of the first part and second part of the radiations impacting the detector plane, wherein variation of the position of the object relative to the object plane of the imaging system along the first axis causes variation of a position of the first spot and of the second spot relative to each other along the second axis.

In some embodiments, a sensor can comprise: a main electrode, positioned on top of the chamber, in contact with the electrically conductive solution, the electrode being submitted to a known potential, a secondary electrode at the bottom of the chamber, carrying the surface to which the molecule can be attached, and an electronic circuit, adapted to measure a current flowing between the electrodes, that comprises a current to voltage amplifier connected to the secondary electrode, a voltmeter adapted to measure an output voltage of the current to voltage amplifier, and a computing circuit adapted to compute an impedance of the well from the measured voltage. In some cases, a sensor can comprise a camera CMOS capable of collecting photons reflected from the beads. In some cases, a sensor can comprise a CMOS capable of measuring impedance for a feature caused by the movement of the beads up and down. In some cases, a chamber is disposed in a device configured to measure the displacement of a bead of the nucleic acid as a function of the concentration of the binding molecule.

An actuator can comprise at least one permanent magnet, which can be controlled to move in translation along the X-X axis. An actuator can comprise two permanent magnets, positioned at equal distance of the X-X axis and having their magnetic poles aligned perpendicular to the X-X axis, the North pole of a magnet facing the South pole of the other. In some cases, a force of the magnet relative to the bead is constant. In some cases, the force of the magnet relative to the bead is increased or decrease. In some embodiments, the force of the magnet is at least 1 piconewton, at least 5 piconewton, at least 10 piconewton, at least 20 piconewton, at least 35 piconewton, at least 70 piconewton or at least 95 piconewton. In some embodiments, the force of the magnet is not more than 100 piconewton. The force of the magnet in the presence of a binding molecule is compared to the force without binding molecule. An example of force of the magnet relative to the bead, may be 1 to 35 piconewton, or more and up to 100 piconewton.

In some embodiments, attaching of a bead can comprise a biotin-streptavidin binding. In some cases, the biotin is conjugated onto one end of the nucleic acid and the streptavidin is conjugated onto the bead.

In some embodiments, attaching a nucleic acid to a plurality of features comprises covalently attaching a DNA oligonucleotide to the bottom of each feature. In some cases, the DNA oligonucleotide has complementarity to the second end of the nucleic acid molecule. In some embodiments, a plurality of nucleic acid molecules is anchored to a bottom of the plurality of features. In some cases, each feature of a chamber comprises a single nucleic acid molecule sequence among the plurality of nucleic acid molecule sequences.

In some embodiments, a single concentration of the binding molecule is added to a chamber. In some cases, the unfolding force of the nucleic acid as a function of the concentration of the binding molecule is calculated for each concentration of the binding molecule.

As disclosed herein, a device can comprise a plurality of features. For examples, a device can comprise at least 100, 1000, 2000, 3000, 4000, 5000, 6000, 7000, 8000, 9000, 10000, 20000, 30000, 40000, 50000, 60000, 70000, 80000, 90000, or greater than 100000 features. As such, individual binding experiments can be performed on a vast number of individual molecules simultaneously.

As disclosed herein, a feature means a binding moietiy at the surface of the flow cell, such moieties are covalently or non-covalently attached at the surface. These features allow the anchoring of the RNA molecules at the surface of the flow cell. These features can either be a protein (an antibody or a streptavidin for example) or an oligonucleotide (similar to a microarray). Covalent attachment of the binding moieties at the surface of the flow cell can be performed by a skilled person and comprises either esterification or click chemistry. In case an oligonucleotide is used, it can be the same sequence for all the features or of different sequence. In some cases, having different sequences composing the features might be advantageous to anchor different RNA molecules at specific position within the flow cell. This allows to map rapidly the different structures within the flowcell. The sequence of the RNA that allows anchoring to the surface can be to be adapted accordingly.

EXEMPLARY EMBODIMENTS

Provided herein is embodiment 1, wherein embodiment 1 comprises a method of screening binding or non-binding molecules to a nucleic acid molecule, the method comprising:

a. attaching a plurality of the nucleic acid molecules to a plurality of beads via one end of the nucleic acid molecule;
b. attaching a plurality of nucleic acid molecules to a plurality of features of a device via a second end of the nucleic acid molecule;
c. contacting a chamber with a library of binding molecules, wherein each member of the library of binding molecules are contacted with a plurality of single nucleic acid molecule in a single chamber;
d. approaching a magnet to cause the plurality of beads to move relative to a bottom surface along an axis of the chamber and measuring a change in bead position via a sensor of the device based on movement of the bead relative to the bottom surface;
e. determining an unfolding force of the nucleic acid molecule in the presence of each member of the library of binding molecules; and
f. selecting members of the library of binding molecules that produce an unfolding force of the nucleic acid molecule that is greater or smaller than an unfolding force of the nucleic acid molecule in the absence of the binding molecule.

Provided herein is embodiment 2, wherein embodiment 2 comprises the method of embodiment 1 further comprising selecting members of the library of binding molecules that do not produce an unfolding force of the nucleic acid molecule that is greater or smaller than an unfolding force of the nucleic acid molecule in the absence of the binding molecule.

Provided herein is embodiment 3, wherein embodiment 3 comprises a method of identifying a chemical signature of optimal binders among a library of binding molecules to a nucleic acid molecule; the method comprising:

a. attaching a plurality of the nucleic acid molecules to a plurality of beads via a first end of the nucleic acid molecule;
b. attaching a plurality of nucleic acid molecules to a plurality of features of a device via a second end of the nucleic acid molecule;
c. contacting a chamber with a library of binding molecules, wherein each member of the library of binding molecules are contacted with a single nucleic acid molecule;
d. approaching a magnet to cause the plurality of beads to move relative to a bottom surface along an axis of the chamber and measuring a change in bead position via a sensor of the device based on movement of the bead relative to the bottom surface;
e. determining an unfolding force of the nucleic acid molecule in the presence of each member of the library of binding molecules;
f. selecting members of the library of binding molecules that produce an unfolding force of the nucleic acid molecule that is greater or smaller than an unfolding force of the nucleic acid molecule in the absence of the binding molecule; and
g. modeling the selected members of the library of binding molecules to identify a chemical signature of optimal binders among the library of binding molecules.

Provided herein is embodiment 4, wherein embodiment 4 comprises the method of any one of the preceeding embodiments, wherein the plurality of features comprises at least 10,000 features.

Provided herein is embodiment 5, wherein embodiment 5 comprises the method of any one of the preceeding embodiments, wherein the sensor of (d) comprises a camera CMOS capable of collecting photons reflected from the beads.

Provided herein is embodiment 6, wherein embodiment 6 comprises the method of any one of the preceeding embodiments, wherein the sensor of (d) comprises a CMOS capable of measuring impedance from the features caused by the movement of the beads, in particular the movement of the beads up and down.

Provided herein is embodiment 7, wherein embodiment 7 comprises the method of any one of the preceeding embodiments, wherein the nucleic acid molecule comprises a DNA molecule, a RNA molecule, a combination thereof.

Provided herein is embodiment 8, wherein embodiment 8 comprises the method of any one of the preceeding embodiments, wherein the nucleic acid molecule is a DNA/RNA hybrid molecule.

Provided herein is embodiment 9, wherein embodiment 9 comprises the method of any one of the preceeding embodiments, wherein the plurality of nucleic acid molecules are the same or different nucleic acid molecules.

Provided herein is embodiment 10, wherein embodiment 10 comprises the method of any one of the preceeding embodiments, wherein a force of the magnet relative to the bead is constant or increased.

Provided herein is embodiment 11, wherein embodiment 11 comprises the method of any one of the preceeding embodiments, wherein the nucleic acid molecule is from about 20 bp to about 350 bp.

Provided herein is embodiment 12, wherein embodiment 12 comprises the method of any one of the preceeding embodiments, wherein the nucleic acid molecule is from about 20 bases to about 350 bases.

Provided herein is embodiment 13, wherein embodiment 13 comprises the method of any one of the preceeding embodiments, wherein the nucleic acid molecule is chemically synthesized.

Provided herein is embodiment 14, wherein embodiment 14 comprises the method of any one of the preceeding embodiments, wherein the nucleic acid molecule is produced via in vitro transcription.

Provided herein is embodiment 15, wherein embodiment 15 comprises the method of any one of the preceeding embodiments, wherein the nucleic acid molecule is produced via polymerase chain reaction.

Provided herein is embodiment 16, wherein embodiment 16 comprises the method of any one of the preceeding embodiments, wherein the binding molecule is a small molecule or a polypeptide.

Provided herein is embodiment 17, wherein embodiment 17 comprises the method of any one of the preceeding embodiments, wherein the device is configured to resolve a difference in unfolding force of from about 0.1 fold to about 30-fold among members of the library of binding molecules.

Provided herein is embodiment 18, wherein embodiment 18 comprises the method of any one of the preceeding embodiments, wherein the attaching of (a) comprises a biotin-streptavidin binding, wherein the biotin is conjugated onto one end of the nucleic acid and the streptavidin is conjugated onto the bead.

Provided herein is embodiment 19, wherein embodiment 19 comprises the method of any one of the preceeding embodiments, wherein the attaching of (b) comprises a DNA oligonucleotide covalently attached to the bottom of each feature, wherein the DNA oligonucleotide has complementarity to the second end of the nucleic acid molecule.

Provided herein is embodiment 20, wherein embodiment 20 comprises a method of determining binding kinetics of a binding molecule to a nucleic acid molecule, the method comprising:

a. attaching a plurality of the nucleic acid molecules to a plurality of beads via a first end of the nucleic acid molecule;
b. attaching a plurality of nucleic acid molecules to a plurality of features of a device via a second end of the nucleic acid molecule;
c. contacting a chamber with increasing concentrations of the binding molecule;
d. applying a magnetic field sufficient to cause each bead of the plurality of beads to move relative to a bottom surface of the chamber and measuring a change in bead position via a sensor of the device based on movement of the bead relative to the bottom surface;
e. determining an unfolding force of the nucleic acid molecule as a function of the concentration of the binding molecule; and
f. calculating the binding kinetics of the binding molecule to the nucleic acid molecule based on the change unfolding force as a function of the amount of the binding molecule.

Provided herein is embodiment 21, wherein embodiment 21 comprises the method of any one of the preceeding embodiments, wherein the unfolding force of the nucleic acid molecule as a function of the concentration of the binding molecule is calculated for each concentration of the binding molecule simultaneously.

Provided herein is embodiment 22, wherein embodiment 22 comprises the method of any one of the preceeding embodiments, wherein the binding molecule has a dissociation constant ($K_D$) of from about 0.01 nM to about 100 mM.

Provided herein is embodiment 23, wherein embodiment 23 comprises a method of determining binding kinetics of a binding molecule to a nucleic acid molecule, the method comprising:

a. contacting the nucleic acid molecule attached to a fixed end of a chamber and a magnetic bead on opposite ends with increasing concentrations of the binding molecule; and
b. determining an unfolding force of the nucleic acid as a function of the concentration of the binding molecule; wherein the nucleic acid molecule is selected from the group consisting of: HIV-1 TAR, preQ1 riboswitch, pre-miR-21, MYC, APOC3, DM1, C9orf72, MAPT, and FMR1.

Provided herein is embodiment 24, wherein embodiment 24 comprises the method of any one of the preceeding embodiments, wherein the binding molecule is a small chemical molecule.

Provided herein is embodiment 25, wherein embodiment 25 comprises the method of any one of the preceeding embodiments, wherein the binding molecule is a polypeptide.

Provided herein is embodiment 26, wherein embodiment 26 comprises the method of any one of the preceeding embodiments, wherein the binding molecule has a dissociation constant ($K_D$) of from about 0.01 nM to about 100 mM.

Provided herein is embodiment 27, wherein embodiment 27 comprises the method of any one of the preceeding embodiments, wherein the chamber is disposed in a device configured to measure the displacement of a bead of the nucleic acid as a function of the concentration of a binding molecule.

Provided herein is embodiment 28, wherein embodiment 28 comprises the method of any one of the preceeding embodiments, wherein the device comprises a plurality of features.

Provided herein is embodiment 29, wherein embodiment 29 comprises the method of any one of the preceeding embodiments, wherein a plurality of nucleic acid molecules is anchored to a bottom of the plurality of features, wherein each feature of a chamber comprises a single nucleic acid molecule sequence among the plurality of nucleic acid molecule sequences.

Provided herein is embodiment 30, wherein embodiment 30 comprises the method of any one of the preceeding embodiments, wherein a single concentration of the binding molecule is added to the chamber, and wherein the unfolding force of the nucleic acid as a function of the concentration of the binding molecule is calculated for each concentration of the binding molecule.

Provided herein is embodiment 31, wherein embodiment 31 comprises the method of any one of the preceeding embodiments, wherein the plurality of features comprises at least 10,000 features.

Provided herein is embodiment 32, wherein embodiment 32 comprises the method of any one of the preceeding embodiments, wherein the nucleic acid molecule comprises HIV-1 TAR, preQ1 riboswitch, pre-miR-2 or DM1, or a viral nucleic acid.

Provided herein is embodiment 33, wherein embodiment 33 comprises the method of any one of the preceeding embodiments, wherein the nucleic acid molecule is preQ1 riboswitch.

Provided herein is embodiment 34, wherein embodiment 34 comprises the method of any one of the preceeding embodiments, wherein the preQ1 riboswitch comprises a mutation, relative to a wild type preQ1 riboswitch, that is selected from the group consisting of: C15U, U7C, A10G, and U6C.

Provided herein is embodiment 35, wherein embodiment 35 comprises a system for practicing the method of any one of the preceeding embodiments.

Provided herein is embodiment 36, wherein embodiment 36 comprises a kit and a container comprising a system for practicing any one of the methods of any one of the preceeding embodiments.

Provided herein is embodiment 37, wherein embodiment 37 comprises an apparatus comprising a system for practicing any one of the methods of any one of the preceeding embodiments.

Provided herein is embodiment 38, wherein embodiment 38 comprises a system for screening binding molecules to a nucleic acid molecule, the system comprising:

a. a plurality of the nucleic acid molecules attached to a plurality of beads via one end of the nucleic acid molecule;
b. a plurality of nucleic acid molecules attached to a plurality of features of a device via a second end of the nucleic acid molecule;
c. a chamber with a library of binding molecules, wherein each member of the library of binding molecules are contacted with a plurality of single nucleic acid molecule in a single chamber;
d. a magnet to cause the plurality of beads to move relative to a bottom surface along an axis of the chamber; and
e. a sensor to measure a change in bead position of the device based on movement of the bead relative to the bottom surface.

Provided herein is embodiment 39, wherein embodiment 39 comprises a system for determining the binding kinetics of a binding molecule to a nucleic acid molecule, the system comprising:

a. a plurality of the nucleic acid molecules attached to a plurality of beads via one end of the nucleic acid molecule;
b. a plurality of nucleic acid molecules attached to a plurality of features of a device via a second end of the nucleic acid molecule;
c. a chamber with a library of binding molecules, wherein each member of the library of binding molecules are contacted with a plurality of single nucleic acid molecule in a single chamber;
d. a magnet to cause the plurality of beads to move relative to a bottom surface along an axis of the chamber; and
e. a sensor to measure a change in bead position of the device based on movement of the bead relative to the bottom surface.

Provided herein is embodiment 40, wherein embodiment 40 comprises a kit comprising:

a. a nucleic acid molecule, or a plurality of the same or of different nucleic acid molecules comprising an orienting sequence at one end and a biotin moiety at the other end;
b. a DNA handle comprising a first reactive group, wherein the DNA handle is capable of hybridizing to the orienting sequence;
c. a feature of a device comprising a second reactive group that is capable of undergoing a chemical reaction with the first reactive group; and
d. a bead or a plurality of beads comprising streptavidin moiety that is capable of binding to the biotin moiety.

Provided herein is embodiment 41, wherein embodiment 41 comprises the kits of the preceeding embodiment further comprising a library of binding molecules.

Provided herein is embodiment 42, wherein embodiment 42 comprises the kits of any one of the preceeding embodiments, wherein the library of binding molecules comprises a library of small molecules, a library of proteins, a library of antibodies, a library of aptamers, advantageously a library comprising binding molecules.

Provided herein is embodiment 43, wherein embodiment 43 comprises the kits of any one of the preceeding embodiments further comprising a buffer comprising a divalent cation in a range of from 1 μM to 1 mM.

Provided herein is embodiment 44, wherein embodiment 44 comprises the kit of any one of the preceeding embodiments, wherein the divalent cation comprises $Mg^{2+}$, $Mn^{2+}$, $Zn^{2+}$, $Fe^{2+}$, $Cu^{2+}$, or $Cd^{2+}$.

Provided herein is embodiment 45, wherein embodiment 45 comprises the kit of any one of the preceeding embodiments, wherein the chemical reaction is an esterification reaction.

Provided herein is embodiment 46, wherein embodiment 46 comprises the kit of any one of the preceeding embodiment, wherein the chemical reaction is a click chemistry.

EXAMPLES

For a better understanding of the present disclosure and of its many advantages, the following examples are given by way of illustration and without limiting the scope of this disclosure.

Example 1: Measuring Binding Affinities for Different Ligands to HIV-1 TAR

Figure 2A:
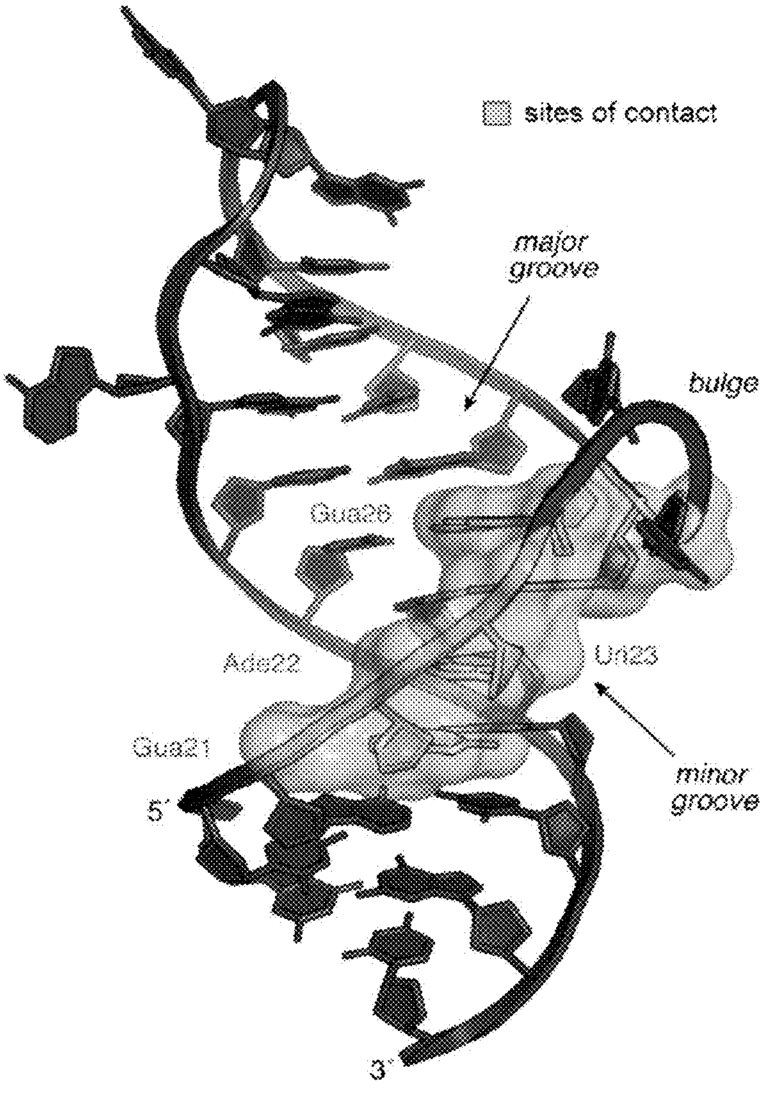
FIG. 2A-2E depict binding affinity of different molecules on HIV-TAR RNA structure.
Figure 2B:
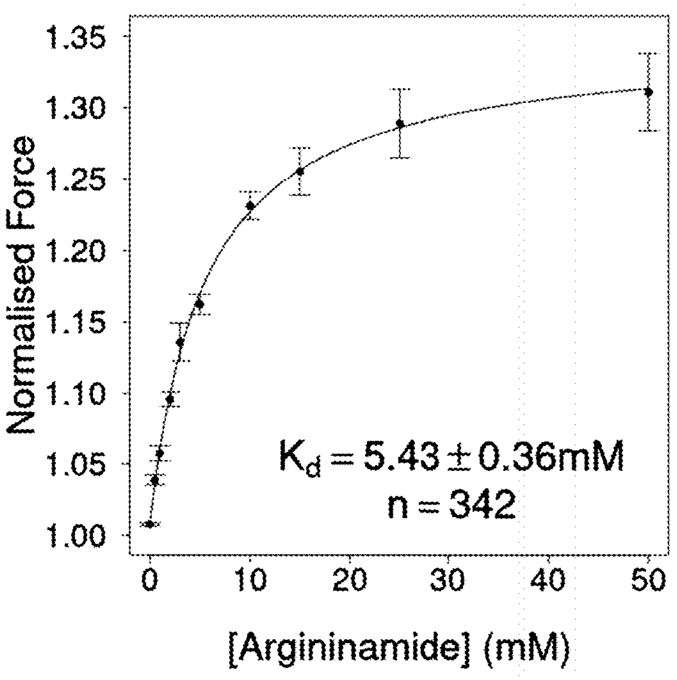

A 59-nucleotide HIV-TAR RNA flanked by RNA/DNA duplexes was attached to a paramagnetic bead on one side and the flowcell on the other end. Ramp experiments showed characteristic traces of unfolding and refolding forces with hysteresis in between (FIG. 2B-2E). Adding 10 mM argininamide increased both the unfolding and refolding force (FIG. 2B), demonstrating that argininamide binding increases the stability of the HIV-TAR RNA molecule. Adding increasing concentrations of argininamide increased the unfolding force and a $K_D$ of 5.43 mM was calculated by fitting the normalized force at maximum unfolding distribution for each bead (FIG. 2B). This demonstrates that the method described herein is suitable to study the binding affinity of small molecules to RNA secondary structures.

Figure 2C:
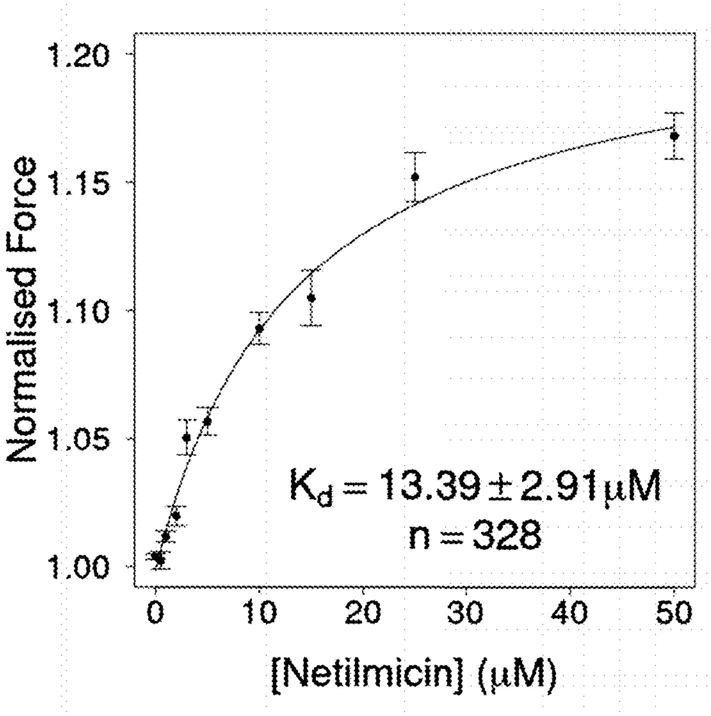
Figure 2D:
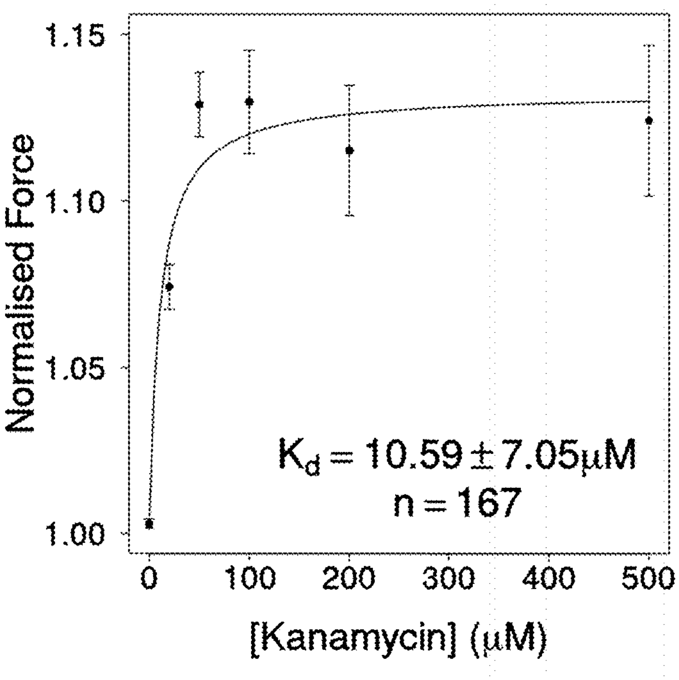
Figure 2E:
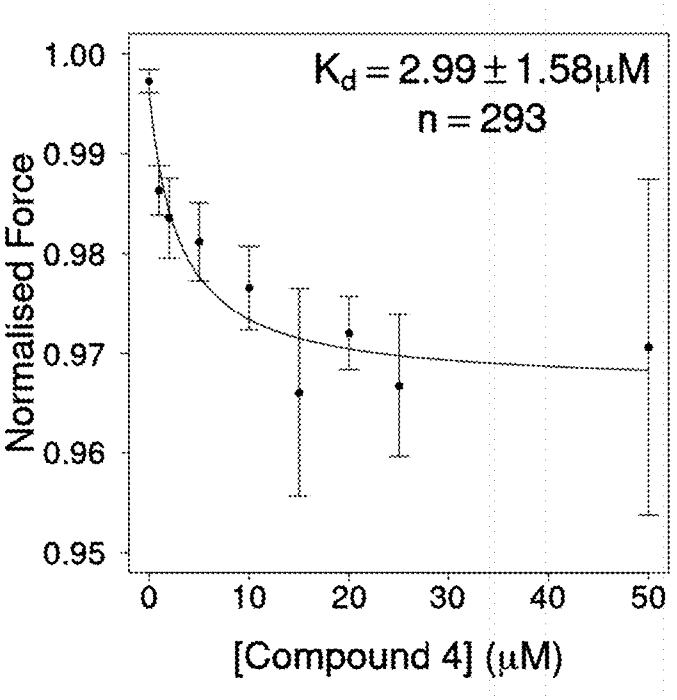

To investigate whether the platform can distinguish between different $K_D$, three additional small molecules were used that are known to bind to the HIV-1 TAR structure with varying binding affinities (FIG. 2C-2E). Netilmicin is a selective binder of HIV-1 TAR with a $K_D$ 1.4 μM and $K_i$~14 μM. Indeed, increasing Netilmicin concentration caused an increase in the unfolding force, and the calculated $K_D$ was around 13.4 μM (FIG. 2C). A non-specific aminoglycoside antibiotic, Kanamycin, can also bind to pyrene-labelled HIV-1 TAR with a $K_D$ of 107 μM. Adding Kanamycin caused an increase in the unfolding force (FIG. 2D). Above 100 μM of Kanamycin, there is a widening of the force distribution (FIG. 2D). Fitting the force at maximum normalized distribution showed an increase in the unfolding force when Kanamycin is present, with a calculated $K_D$ of 10 μM. 3-Amino-6-methyl-N-(3-(trifluoromethyl)phenyl) thieno[2,3-b]pyridine-2-carboxamide, referred to Compound 4, which is a specific binder of HIV-1 TAR with a $K_D$ of 2.4 μM, was also tested. Adding Compound 4 caused a decrease in the unfolding force (FIG. 2E), which could be the result of non-canonical binding of the molecule to the lower bulge, destabilizing the HIV-1 TAR structure. Fitting the changes in the unfolding force resulted in a $K_D$ of 2.99 μM.

In summary, the platform described herein was used to determine the binding affinity of different small molecules. From ramp experiments, the system detects changes in unfolding and refolding forces if the ligand binding causes a change in RNA structure stability. The differences in binding affinity ($K_D$) can be calculated for different small molecules, making the platform suitable for screening libraries of drugs against specific RNA targets.

Example 2—Binding of Ligand to PreQ1 Riboswitch

Figure 3A:
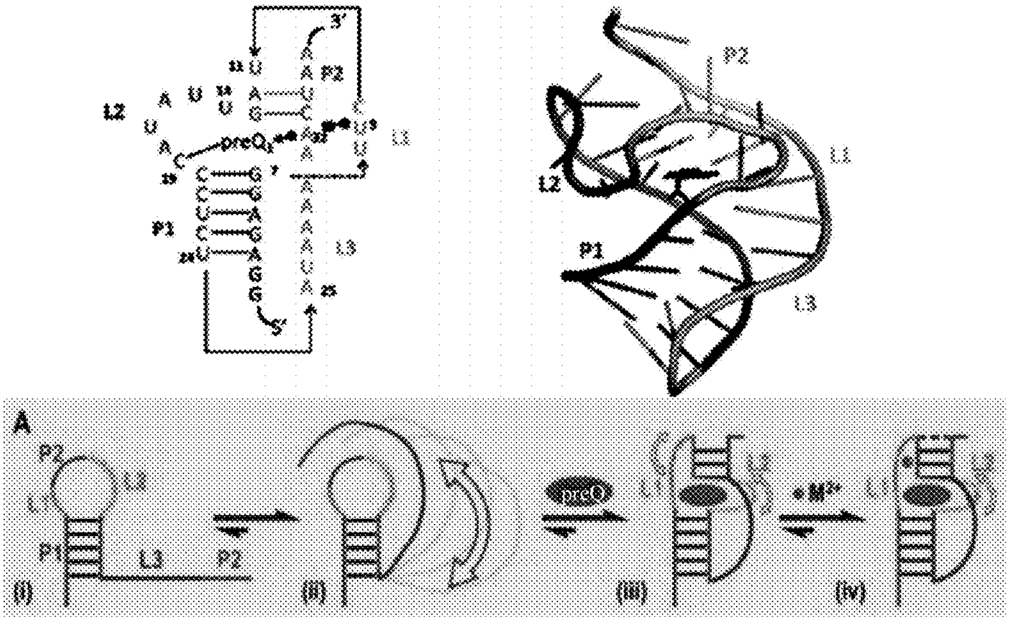
FIG. 3A-3K depict molecular dynamics of preQ1 riboswitch ligand binding.

This example demonstrates binding of ligand to Bsu PreQ1 riboswitch. The Bsu riboswitch exhibits a major population of 'pre-folded' state where the 3' tail transiently interacts with the P1-L1 stem-loop (FIG. 3A). Given the conformational rearrangement upon ligand binding of the Bsu preQ1 riboswitch, we observed a change in the unfolded and folded state under a constant-force experiment.

Figure 3B:
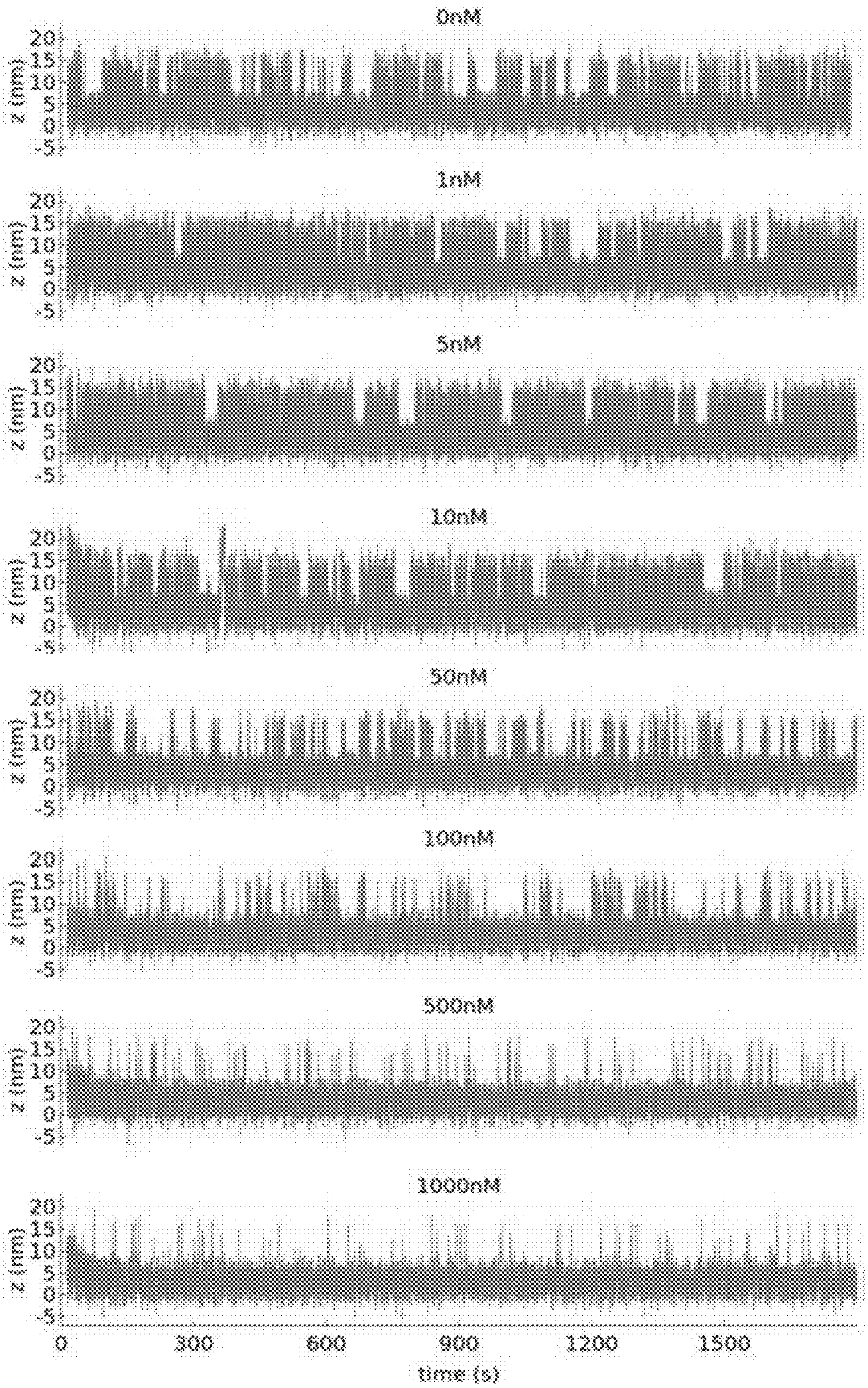
Figure 3C:
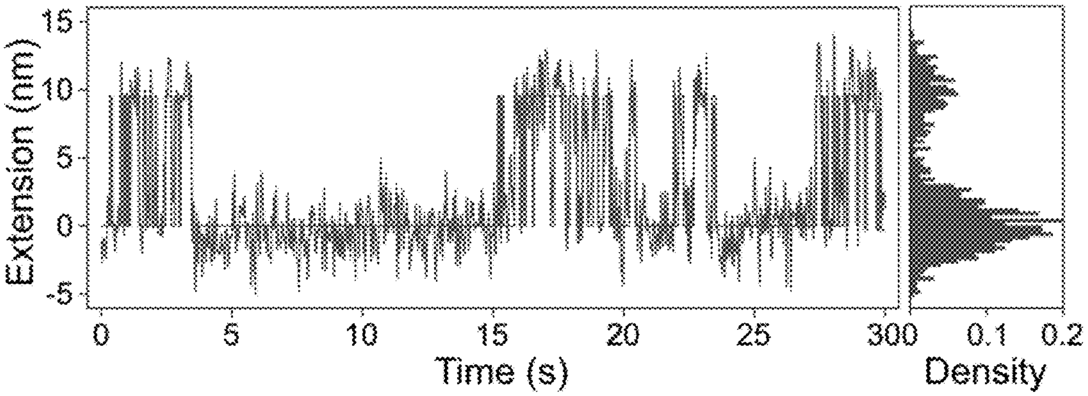
Figure 3D:
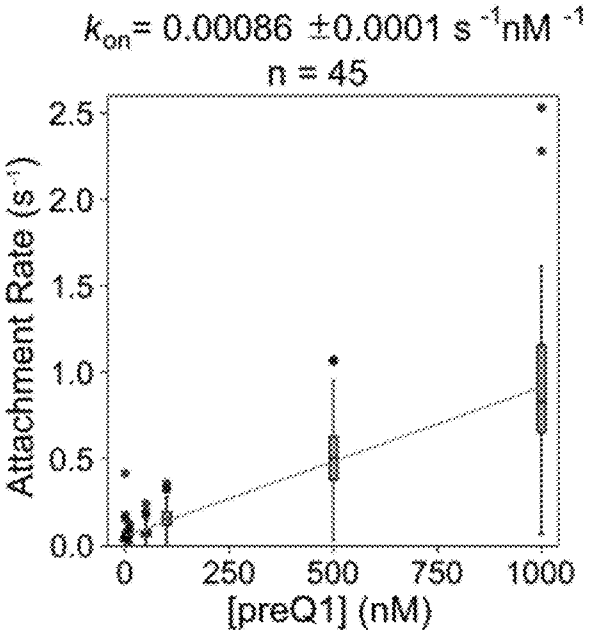
Figure 3E:
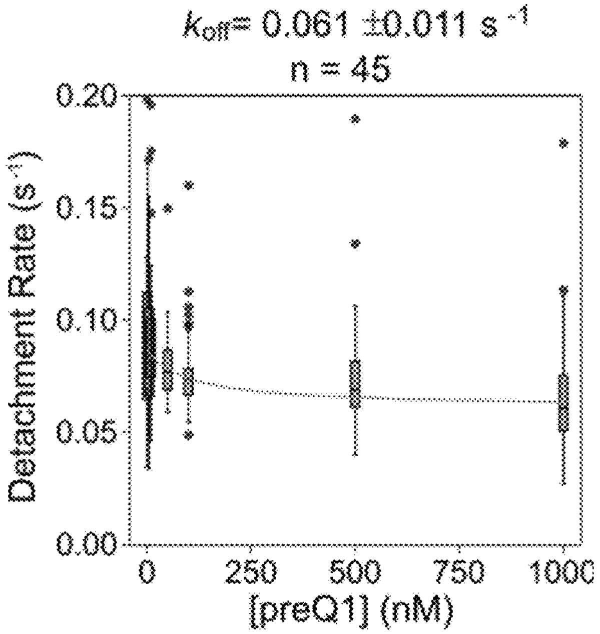
Figure 3F:
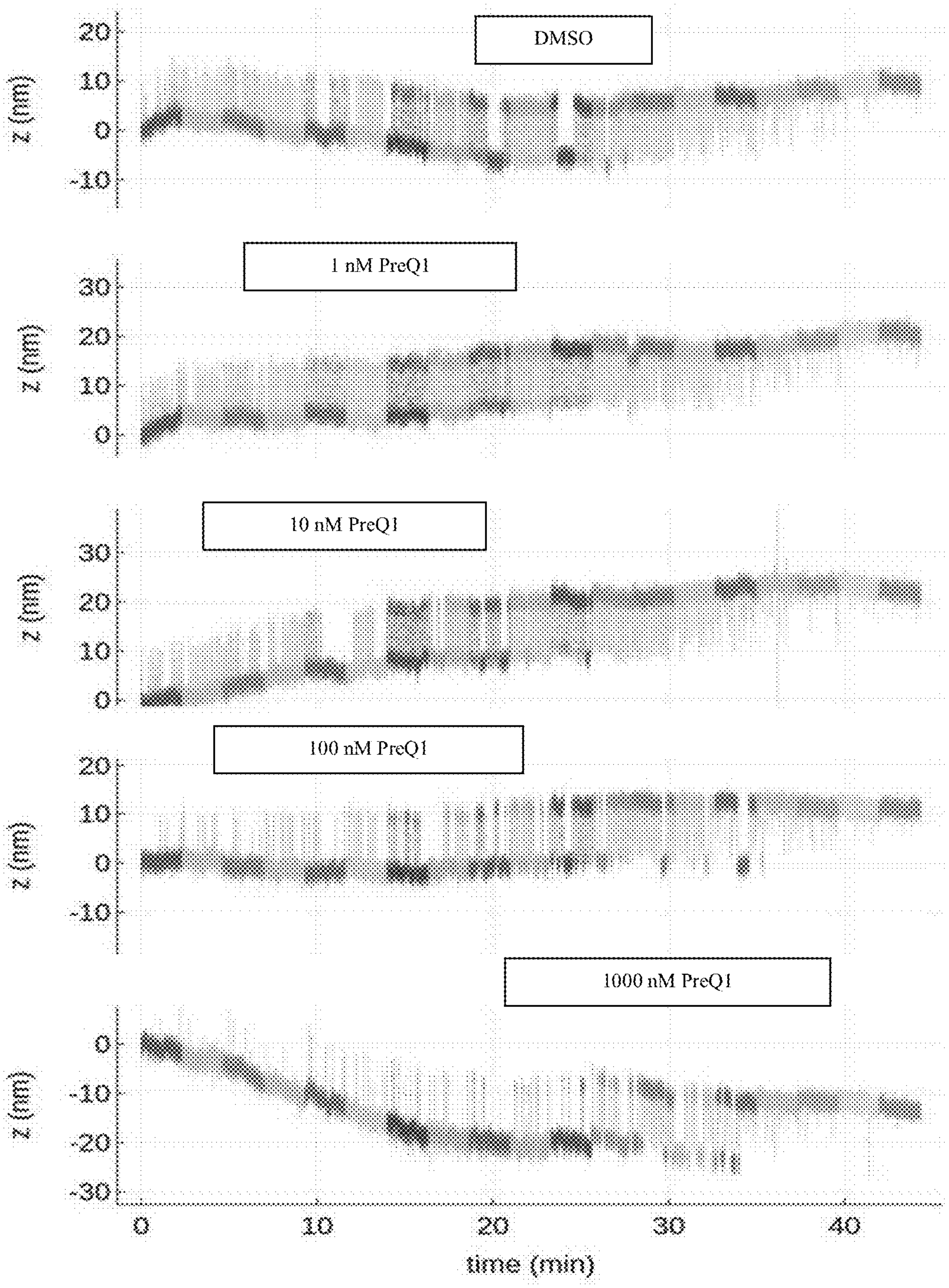
Figure 3G:
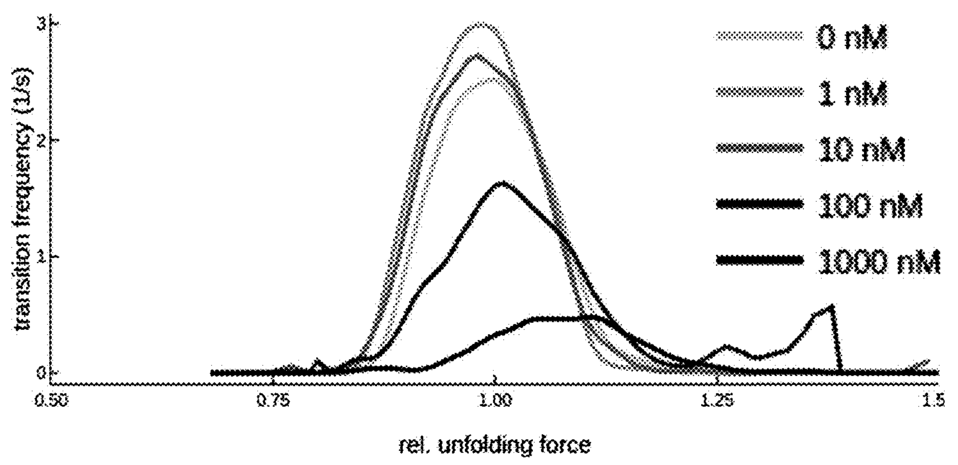
Figure 3H:
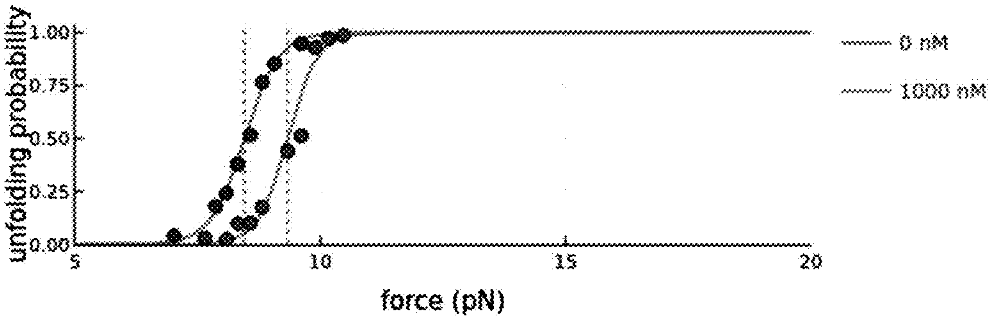
Figure 3I:
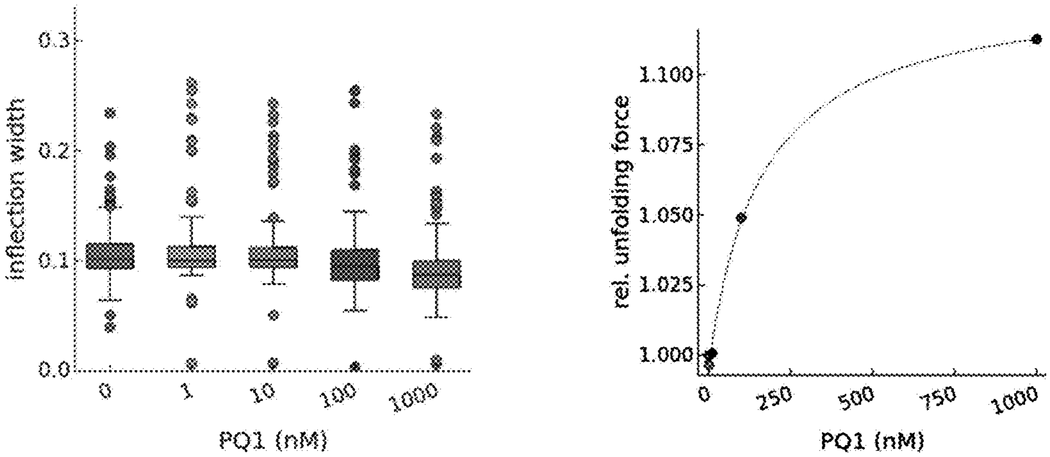

To study the molecular dynamics of the preQ1 riboswitch using the platform described herein, wild type (WT) Bsu riboswitch was attached to the flowcell as described in Example 1. A step constant-force experiments were then performed, where the molecule is kept at a constant force for a given amount of time before increasing the force in a stepwise manner from lower to higher forces (FIG. 3B). The z position of the bead was recorded and at forces closer to equilibrium, the molecule transitioned between the folded and unfolded state (FIG. 3B). The force was maintained constant for five minutes at the equilibrium force (where the molecule spends as much time in the unfolded versus folded state) and various concentrations of the preQ1 ligand were tested. The binding of the ligand to the structure (arrows shown in representative binding analysis curve of FIG. 3C) was monitored in real time and at the level of the single molecule. A binding which causes the structure to remain in the folded state for more than 3 seconds was recorded. The $k_{on}$ calculated by dividing the number of events observed when the ligand is bound to the RNA structure over the time of experiment at a given concentration of the ligand. The RNA is considered bound to a ligand (here preQ1 ligand) when it stays folded for longer than 3.3 seconds. By testing different concentrations, the $k_{on}$ of the molecule was measured (FIG. 3D). The $k_{off}$ is inverse of the length of time when the RNA structure is bound by a ligand. Accordingly, a duration, when the ligand left the RNA structure (star) as the RNA structure went back to rapid transition between folded and unfolded state, was observed. The duration of this folded state allows to measure the $k_{off}$ of the ligand (FIG. 3E). The $k_{on}$ is dependent on the ligand concentration whereas the $k_{off}$ is not. For each force, the raw data was fitted to two different states using Hidden Markov model (FIG. 3B), and the fraction of time for which each molecule is present at the folded state was calculated over the time at each force step. The fraction was plotted against the force for each step, and the equilibrium force (inflection point) was determined for each molecule when the molecule spent 50% of the time at each state (FIG. 3F). The half-width of the force can also be determined by calculating 1/e (e=Euler's number) on either side of the inflection point, which indicates the force range where the molecule is bistable and transitions from folded and unfolded state (FIG. 3F). The transition frequency was calculated for each of the force steps recorded and plotted again the normalized force, corresponding to the equilibrium force for each bead in control conditions (FIG. 3G).

Figure 3J:
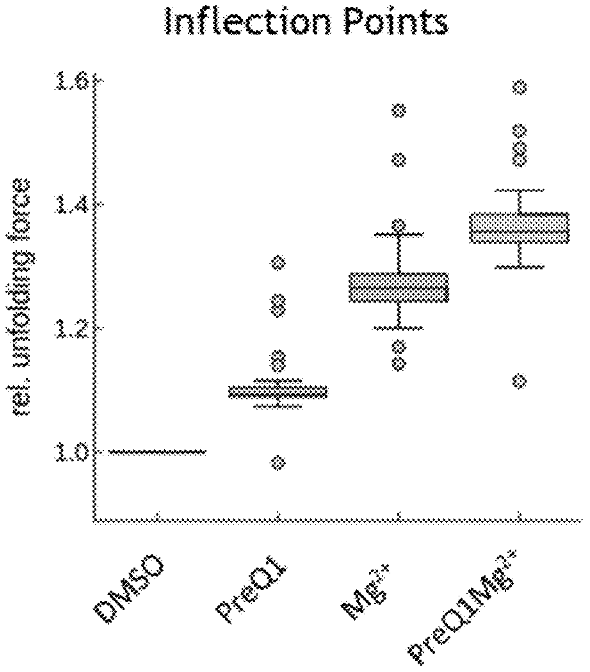
Figure 3K:
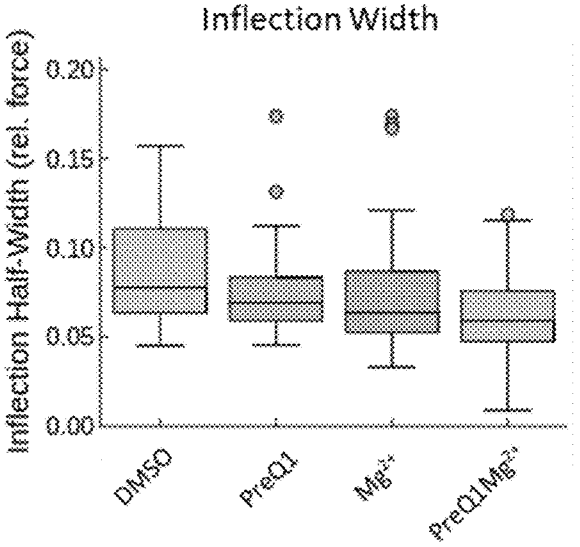

To determine whether the presence of $Mg^{2+}$ had an effect on folding confirmation, various concentrations of $Mg^{2+}$ were added to each flowcell. Indeed, adding 1 mM $Mg^{2+}$ alone increased the unfolding equilibrium force of the same molecule without affecting the force range (FIG. 3J), and the transition frequency decreased at equilibrium force (FIG. 3K), indicating a stabilization effect of the $Mg^{2+}$ on the preQ1 RNA structures in absence of the ligand. The addition of 1 μM of preQ1 ligand (higher than the described value for the preQ1 $K_D$) also increased the unfolding equilibrium force and decreased transition frequency, although to a lesser extent (FIG. 3J and FIG. 3K). The addition of both ligand and cation showed an additive effect (FIG. 3J and FIG. 3K), indicating that both molecules bind the RNA structure at different positions. For the subsequent experiments, 1 mM $Mg^{2+}$ was added in all buffers.

To study the effect of preQ1 ligand binding to the riboswitch, constant-force step experiments were performed with increasing concentration of preQ1 ligand (FIG. 3B). Quantification showed that increasing concentrations of preQ1 increased equilibrium force of the riboswitch (FIG. 3F) as well as decreased the transition frequency (FIG. 3F). The $K_D$ (162 nM) was calculated by fitting the equilibrium force at each concentration, and was compared to results obtained by smFRET (134+/−48 nM).

Constant-force experiments were performed at 9.6 pN (median of fitted equilibrium force for all beads in control conditions) for a long period of time (30-60 min, FIG. 3G) with increasing concentrations of preQ1 ligand. The molecule was detected to transit between folded and unfolded states, and two different dynamics were observed: (i) the fast switching between folded and unfolded states (~8-10 transition/s) and (ii) a longer period where the molecule remains folded (FIG. 3G). The probability of prolonged folded state increased with preQ1 concentration. Binding by a ligand was defined when the molecule remains folded for more than 3.3 s, whereas when the ligand is not bound, the molecule transits rapidly between the two states. The mean time for each ligand-bound event (folded-states) at each concentration was calculated and the $K_{off}$(one per mean time) showed that it is not affected by the ligand concentration (FIG. 311), with a value of 0.11 $s^{-1}$. The attachment rate was calculated by dividing the number of binding events by the time the molecule spent in the folded state without attachment (during rapid transition) for different concentrations. Hence, the $K_{on}$, calculated by fitting the attachment rate, was 0.0015 $^{-1}$ $nM^{-1}$ (FIG. 311). Therefore, the $K_D$ at 9.6 pN was calculated by $K_{off}/K_{on}$, which was 73 nM.

In summary, the platform described herein demonstrated the capacity to study the dynamics of small molecule binding to RNA structures by using constant-force experiments. The attachment and detachment rates can be deduced from this type of experiments which give more insights into the binding kinetics of the ligand. Consequently, the platform is also suitable to study detailed single molecule folding dynamics.

Example 3—Effect of PreQ1 Mutations on Ligand Binding

Figure 4A:
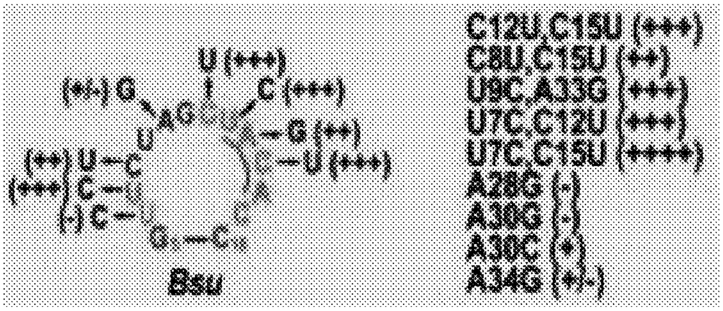
FIG. 4A-4G depict the effect of preQ1 RNA mutations on the binding affinity of preQ1 ligand.

This example demonstrates that the platform described herein can resolve the effect of mutations to a nucleic acid scaffold on ligand binding. The preQ1 riboswitch has several point substitutions that modify affinity to the preQ1 ligand (FIG. 4A). To demonstrate the platform described herein can be used to report changes in the binding affinity using different RNA substrates, we selected four mutants that either increase or decrease the binding affinity (Table 5).

TABLE 5

Effect of PreQ1 mutation on binding affinity

| Molecule | Effect | $K_D$ |
|---|---|---|
| WT | n.a. | 87.8 nM |
| C15U | Increase versus wt | 5.35 nM |
| U7C + C15U | Greatly Increase versus wt | 17.72 nM |
| A10G | Decrease versus wt | 34.67 μM |
| U6C | Abolished versus WT | N/A |

NA or n.a. means not applicable.

Figure 4B:
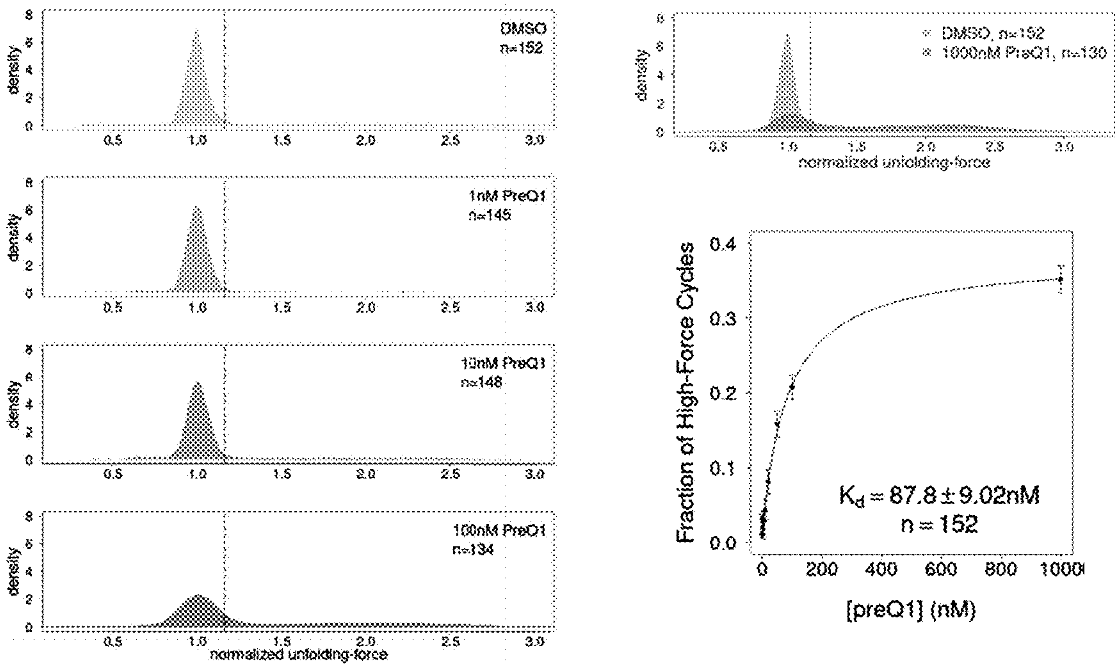

The WT preQ1 riboswitch was used as a reference (FIG. 4B). Using ramp analysis, the unfolding force distribution showed a widening of the distribution (FIG. 4B). The peak around the reference force decreased while there was an increase in the proportion of cycles that have a higher unfolding force. The higher force cycles can represent the binding of the ligand and formation of the pseudoknot. The fraction of cycles that have an unfolding force greater than 95% confidence interval of each bead was calculated in control conditions (FIG. 4B). Fitting the high-force fraction provided a calculated $K_D$ of 87.8+/−9.02 nM (FIG. 4B). This is similar to the $K_D$ calculated in Example 2 from the constant force experiment at 9.6 pN.

Figure 4C:
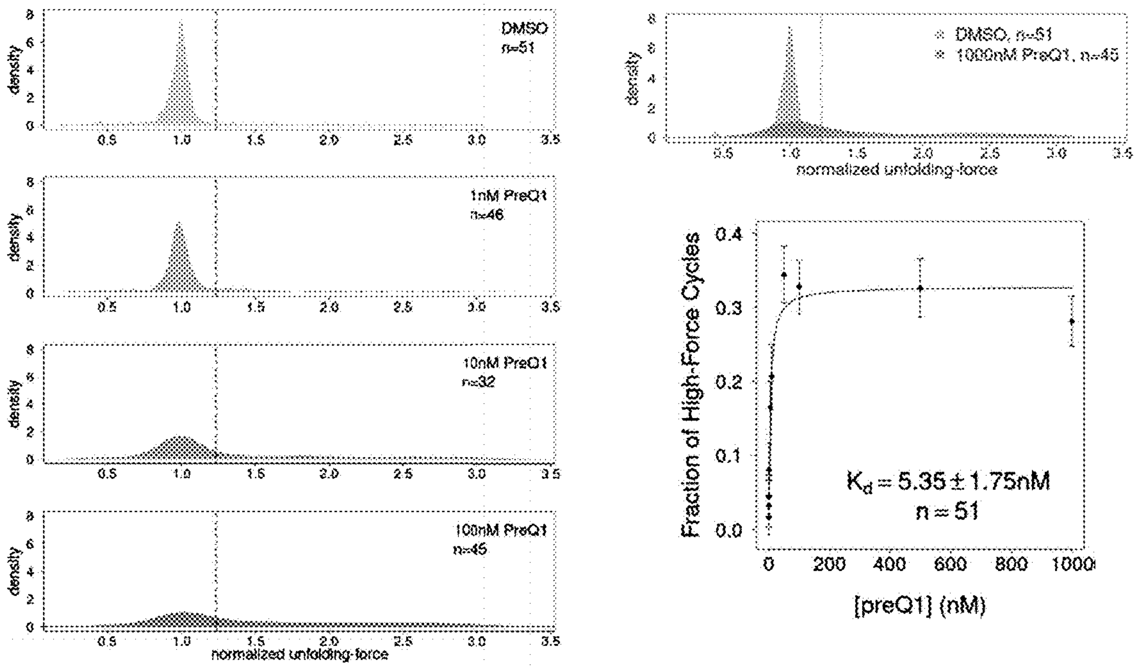
Figure 4D:
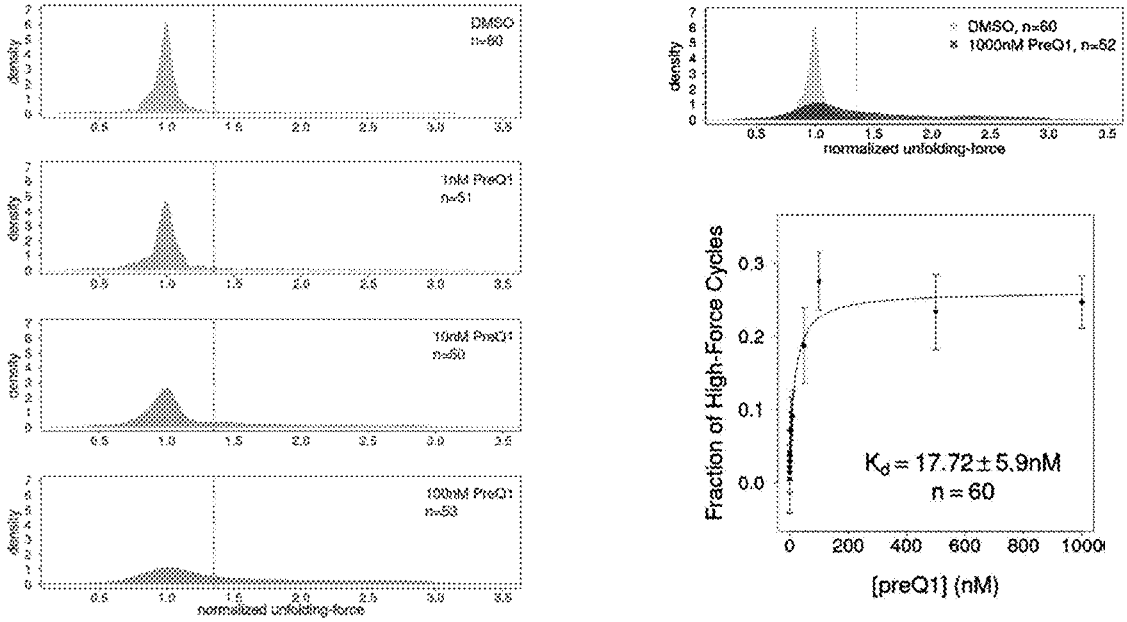

Having established a reference point, the four different mutants were used to study the effect on preQ1 binding (FIG. 4C-4G). Ramp analysis of the C15U mutant showed similar behavior to the WT, with an increase in the high-force fraction upon preQ1 binding (FIG. 4C). Fitting the high-force fraction showed a $K_D$ of 5.35+/−1.75 nM (FIG. 4C). The double mutant U7C, C15U also displayed an increase in $K_D$ (FIG. 4D, 17.72+/−5.9 nM), with a higher $K_D$ than the C15U mutant. The difference could be due to the $Mg^{2+}$ used. Nonetheless, the platform was able to distinguish a 3-fold differences in $K_D$, which is less apparent in platforms like SPR or fluorescent titration.

Figure 4E:
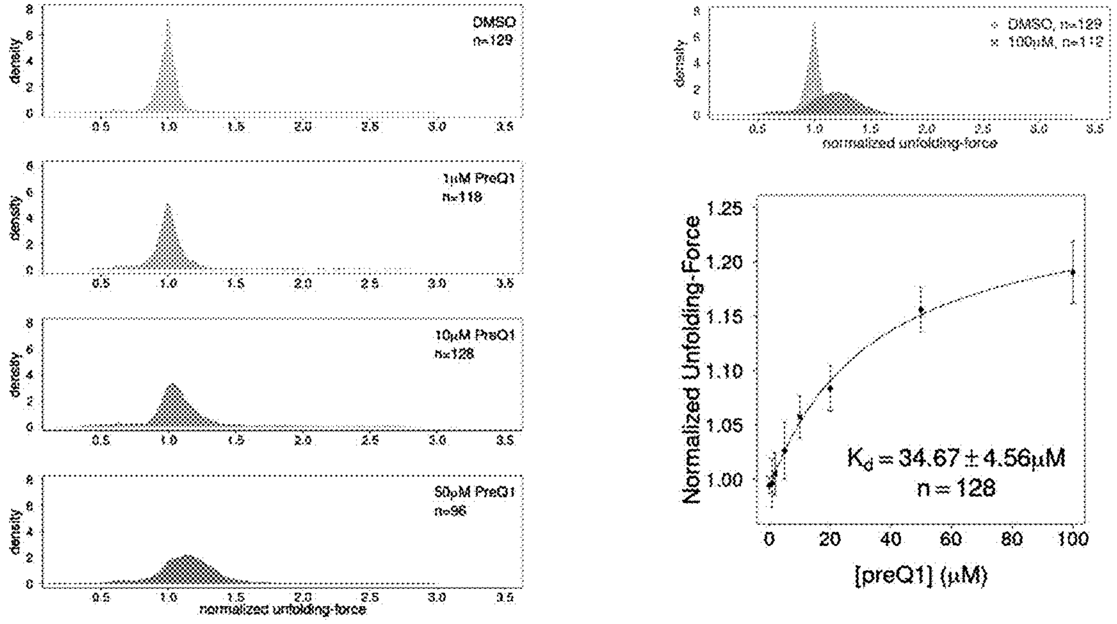
Figure 4F:
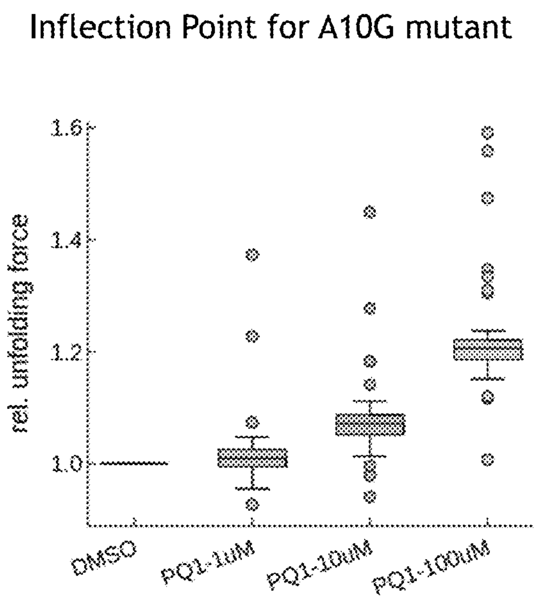

The third mutant, A10G, was shown to decrease the binding affinity of preQ1. Indeed, the effect of unfolding force was seen in a micromolar range instead of nanomolar (FIG. 4E). The unfolding force distribution also resulted in a change. With this mutant, the whole distribution was shifted towards higher forces, instead of having two different fractions (FIG. 4E). This suggests that the ligand could slightly stabilize the existing structure but probably doesn't allow the formation of the pseudoknot, which is harder to unfold. The maximum unfolding force density for each bead was used to fit the $K_D$ (as in Example 1), and the $K_D$ was 34.67+/−4.56 μM, around a 400-fold increase compared with WT (FIG. 4E). The constant-force step experiment also reflected the changes in the equilibrium force in micromolar range (FIG. 4F).

Figure 4G:
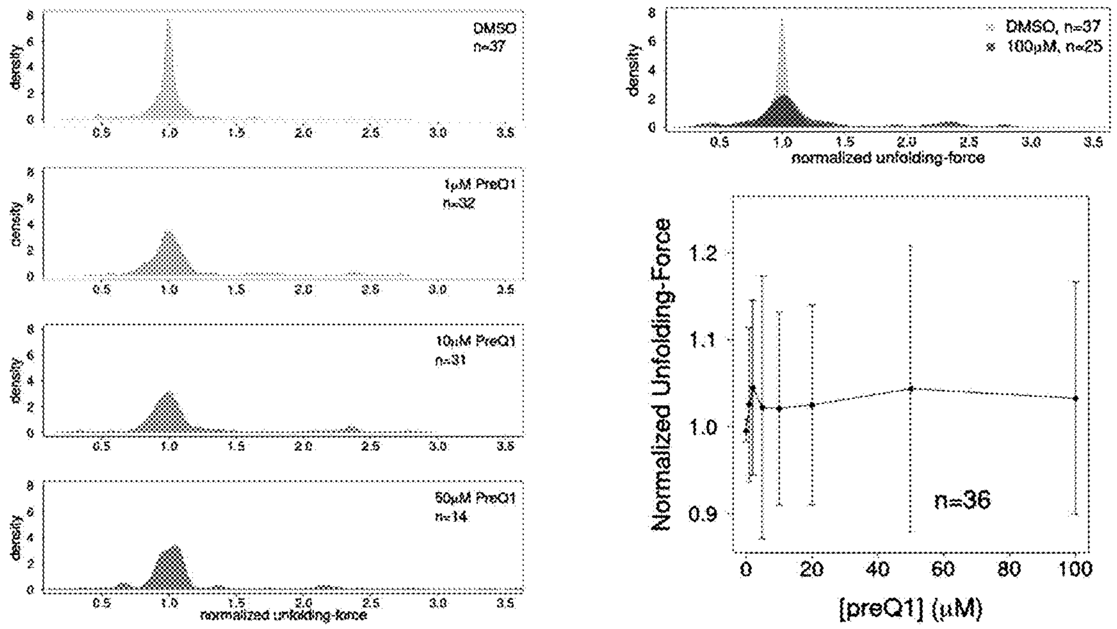

The last mutant, U6C, abolished the ligand binding. The unfolding force distribution appeared as a widening of the peak but the maximum peak did not change (FIG. 4G). Neither fitting the maximum density (FIG. 4G) nor the high-force density resulted in a $K_D$ value, indicating that the U6C mutant abolishes the binding of the preQ1 ligand.

In summary, the platform described herein was able to detect binding affinities ranging from 3- to 400-fold differences. Thus, the platform is useful for studying the effect of sequence mutations on small molecule binding. It can also be used to determine the specificity of a single small molecule on a library of RNA molecules.

Example 4—Measuring Interactions Between Pre-miR-21 and Dicer Protein

Pre-miR-21 and pre-miR-21-bp mutants are used as substrates to measure the effect of Dicer on the folding kinetics. Dicer is a double-strand-specific ribonuclease that binds the pre-miRNAs and cleaves them to generate mature miRNAs. Adding 20 nM of full-length Dicer without magnesium causes the binding of the protein to the structure without further processing of the structure. Binding of Dicer to the pre-miR-21 structure occurs with an increase in the unfolding force. Binding to the mutant form of pre-miR-21-bp (the mutant introduces mutation that abolishes the bulge required for Dicer binding) does not occur. Therefore, the platform described herein is useful for detecting interaction between an RNA scaffold and an RNA binding protein.

In summary, platform described herein allows for studying of the interaction not only between nucleic acid and small molecules but also between protein and nucleic acid. The next step will be to use binding protein to the secondary structure and see if the presence of small molecules can affect this interaction. Therefore, the platform can be used to study inhibition or competition between different molecules.

While exemplary embodiments have been shown and described herein, it will be obvious to those skilled in the art that such embodiments are provided by way of example only. Numerous variations, changes, and substitutions will occur to those skilled in the art. It should be understood that various alternatives to the embodiments described herein may be employed. It is intended that the following claims define the scope of the disclosure and that methods and structures within the scope of these claims and their equivalents be covered thereby.

What is claimed is:

1. A method of screening a library of molecules at single molecule resolution for binding to one or more nucleic acid molecules from a plurality of nucleic acid molecules using a device, wherein each nucleic acid molecule of the plurality of nucleic acid molecules has a first end, a second end, and a secondary structure or a tertiary structure, and wherein the device comprises:

(i) a chamber disposed within the device, wherein the chamber comprises a bottom surface that comprises a plurality of features, (ii) a sensor, and (iii) a mechanism for exerting force;

the method comprising:

(a) attaching the first end of each nucleic acid molecule of the plurality of nucleic acid molecules to a bead, thereby forming a plurality of bead-conjugated nucleic acid molecules;

(b) attaching the second end of each nucleic acid molecule in the plurality of bead-conjugated nucleic acid molecules to a feature among the plurality of features, thereby forming a plurality of immobilized bead-conjugated nucleic acid molecules, wherein each immobilized bead-conjugated nucleic acid molecule of the plurality of immobilized bead-conjugated nucleic acid molecules is positioned along an axis perpendicular to the bottom surface of the chamber of the device;

(c) determining a force required to unfold the secondary structure or the tertiary structure of each nucleic acid by:

(i) applying a force via the mechanism for exerting force to each bead in the plurality of immobilized bead-conjugated nucleic acid molecules, wherein the force is applied perpendicular to the bottom surface of the chamber of the device and is in an amount sufficient to unfold the secondary structure or the tertiary structure of each nucleic acid molecule, thereby resulting in a change in position of each bead along the axis perpendicular to the bottom surface of the chamber, and ii) measuring the change in position of each bead along the axis, relative to the bottom surface of the chamber, using the sensor of the device, thereby determining the force required to unfold the secondary structure or the tertiary structure of each nucleic acid molecule among the plurality of nucleic acid molecules;

(d) determining a force required to unfold the secondary structure or the tertiary structure of each nucleic acid of the plurality of nucleic acid molecules in the presence of the library of molecules by contacting the plurality of immobilized bead-conjugated nucleic acid molecules with the library of molecules and repeating step (c), and (e) identifying one or more members of the library of molecules that bind to one or more nucleic acid molecules among the plurality of nucleic acid molecules based on a differential between: the force required to unfold the secondary structure or the tertiary structure of each nucleic acid molecule in the presence of the one or more members of the library of molecules determined in (d), and the force required to unfold the secondary structure or the tertiary structure of each nucleic acid molecule in the absence of the one or more members of the library of molecules determined in (c), whereby the one or more members of the library of molecules that produce the differential are the one or more member that bind to the one or more nucleic acid molecules.

2. The method of claim 1, further comprising identifying one or more members of the library of molecules that do not bind to one or more nucleic acid molecules among the plurality of nucleic acid molecules, wherein the one or more members of the library that do not bind to one or more nucleic acid molecules among of the plurality of nucleic acid molecules do not produce the differential between the force required to unfold the secondary structure or the tertiary structure of each nucleic acid molecule in the presence of the one or more members of the library of molecules and the force required to unfold the secondary structure or the tertiary structure of each nucleic acid molecule in the absence of the one or more members of the library of molecules.

3. The method of claim 1, wherein each nucleic acid molecule among the plurality of nucleic acid molecules is the same molecule, and wherein the method further comprises modeling the one or more members of the library of molecules that bind to the nucleic acid molecule to identify a chemical signature of optimal binders among the library of molecules.

4. The method of claim 1, wherein the plurality of features comprises at least 10,000 features.

5. The method of claim 1, wherein the sensor comprises a camera CMOS capable of collecting photons reflected from the beads.

6. The method of claim 1, wherein the plurality of nucleic acid molecules are DNA molecules, RNA molecules, or DNA/RNA hybrid molecules.

7. The method of claim 1, wherein the plurality of nucleic acid molecules are different nucleic acid molecules relative to each other.

8. The method of claim 1, wherein the force applied to each bead is constant.

9. The method of claim 1, wherein the force applied to each bead increases or decreases in multiple cycles.

10. The method of claim 1, wherein each nucleic acid molecule among the plurality of nucleic acid molecules is from about 20 bp to about 350 bp.

11. The method of claim 1, wherein each nucleic acid molecule among the plurality of nucleic acid molecules is chemically synthesized or is produced via in vitro transcription.

12. The method of claim 1, wherein the library of molecules are a library of small molecules having a molecular weight of less than 10000 daltons or a library of polypeptides.

13. The method of claim 1, wherein the device is configured to resolve a differential of from about 0.1-fold to about 30-fold between the force required to unfold the secondary structure or the tertiary structure of each nucleic acid molecule in the presence of the library of molecules and the force required to unfold the secondary structure or the tertiary structure of each nucleic acid molecule in the absence of the library of molecules.

14. The method of claim 1, wherein the one or more members of the library of molecules that bind to a nucleic acid molecule among the plurality of nucleic acid molecules have a dissociation constant ($K_D$) of from about 0.01 nM to about 100 mM.

15. The method of claim 1, wherein a nucleic acid molecule among the plurality of nucleic acid molecules is selected from the group consisting of: HIV-1 TAR, preQ1 riboswitch, pre-miR-21, MYC, APOC3, DM1, C9orf72, MAPT, and FMR1.

16. The method of claim 1, wherein the attaching of (a) comprises a biotin-streptavidin conjugation, wherein the biotin is present on the first end of each nucleic acid molecule and the streptavidin is present on each bead.

17. The method of claim 1, wherein the attaching of (b) comprises hybridization of the second end of each nucleic acid molecule among the plurality of nucleic molecules to a DNA oligonucleotide covalently attached to the feature.

18. The method of claim 1, wherein the mechanism for exerting force exerts magnetic force.

* * * * *

SEQUENCE LISTING

```
Sequence total quantity: 53
SEQ ID NO: 1           moltype = RNA  length = 52
FEATURE                Location/Qualifiers
source                 1..52
                       mol_type = other RNA
                       organism = synthetic construct
SEQUENCE: 1
ggctctggtt agaccagatc tgagcctggg agctctctgg ctaactaggg cc         52
```

-continued

```
SEQ ID NO: 2           moltype = RNA  length = 59
FEATURE                Location/Qualifiers
source                 1..59
                       mol_type = other RNA
                       organism = synthetic construct
SEQUENCE: 2
tagcttatca gactgatgtt gactgttgaa tctcatggca acaccagtcg atgggctgt   59

SEQ ID NO: 3           moltype = RNA  length = 34
FEATURE                Location/Qualifiers
source                 1..34
                       mol_type = other RNA
                       organism = synthetic construct
SEQUENCE: 3
agaggttcta gctacaccct ctataaaaaa ctaa                              34

SEQ ID NO: 4           moltype = RNA  length = 52
FEATURE                Location/Qualifiers
source                 1..52
                       mol_type = other RNA
                       organism = synthetic construct
SEQUENCE: 4
ggcgacattt gtaattcctg gaccgatact tccgtcagga cagaggttgc ca          52

SEQ ID NO: 5           moltype = RNA  length = 70
FEATURE                Location/Qualifiers
source                 1..70
                       mol_type = other RNA
                       organism = synthetic construct
SEQUENCE: 5
gggaggacga tgcgggaact caccgggaag aagcccgttc cgtcacagac atgttccgca  60
tcgtcctccc                                                         70

SEQ ID NO: 6           moltype =   length =
SEQUENCE: 6
000

SEQ ID NO: 7           moltype =   length =
SEQUENCE: 7
000

SEQ ID NO: 8           moltype =   length =
SEQUENCE: 8
000

SEQ ID NO: 9           moltype =   length =
SEQUENCE: 9
000

SEQ ID NO: 10          moltype =   length =
SEQUENCE: 10
000

SEQ ID NO: 11          moltype =   length =
SEQUENCE: 11
000

SEQ ID NO: 12          moltype =   length =
SEQUENCE: 12
000

SEQ ID NO: 13          moltype =   length =
SEQUENCE: 13
000

SEQ ID NO: 14          moltype =   length =
SEQUENCE: 14
000

SEQ ID NO: 15          moltype =   length =
SEQUENCE: 15
000

SEQ ID NO: 16          moltype = RNA  length = 106
FEATURE                Location/Qualifiers
source                 1..106
                       mol_type = other RNA
                       organism = synthetic construct
SEQUENCE: 16
```

-continued

```
tcggcgatct acgcagcgac atatatggcg acatttgtaa ttcctggacc gatacttccg  60
tcaggacaga ggttgccata acaacactct cctcatctgt ctctcc                 106

SEQ ID NO: 17          moltype = RNA  length = 120
FEATURE                Location/Qualifiers
source                 1..120
                       mol_type = other RNA
                       organism = synthetic construct
SEQUENCE: 17
tcggcgatct acgcagcgac atatgggagg acgatgcggg aactcaccgg gaagaagccc  60
gttccgtcac agacatgttc cgcatcgtcc tccctaacca ctctcctcat ctgtctctcc  120

SEQ ID NO: 18          moltype = RNA  length = 109
FEATURE                Location/Qualifiers
source                 1..109
                       mol_type = other RNA
                       organism = synthetic construct
SEQUENCE: 18
tcggcgatct acgcagcgac atatatggct ctggttagac cagatctgag cctgggagct  60
ctctggctaa ctagggccta acaaccactt cctaatctgt catcttctg              109

SEQ ID NO: 19          moltype = RNA  length = 91
FEATURE                Location/Qualifiers
source                 1..91
                       mol_type = other RNA
                       organism = synthetic construct
SEQUENCE: 19
tcggcgatct acgcagcgac atatatagag gttctagcta caccctctat aaaaaactaa  60
taacaaccac ttcctaatct gtcatcttct g                                 91

SEQ ID NO: 20          moltype = RNA  length = 116
FEATURE                Location/Qualifiers
source                 1..116
                       mol_type = other RNA
                       organism = synthetic construct
SEQUENCE: 20
tcggcgatct acgcagcgac atatattagc ttatcagact gatgttgact gttgaatctc  60
atggcaacac cagtcgatgg gctgttaaca accacttcct aatctgtcat cttctg      116

SEQ ID NO: 21          moltype = RNA  length = 120
FEATURE                Location/Qualifiers
source                 1..120
                       mol_type = other RNA
                       organism = synthetic construct
SEQUENCE: 21
tcggcgatct acgcagcgac atatatctgc tgctgctgct gctgctgctg ctgctgctgc  60
tgctgctgct gctgctgctg ctgctgctgt aacaaccact tcctaatctg tcatcttctg  120

SEQ ID NO: 22          moltype = RNA  length = 120
FEATURE                Location/Qualifiers
source                 1..120
                       mol_type = other RNA
                       organism = synthetic construct
SEQUENCE: 22
tcggcgatct acgcagcgac atatatttgt ataacctcaa taatatggtt tgagggtgtc  60
taccaggaac cgtaaaatcc tgattacaat aacaaccact tcctaatctg tcatcttctg  120

SEQ ID NO: 23          moltype = RNA  length = 93
FEATURE                Location/Qualifiers
source                 1..93
                       mol_type = other RNA
                       organism = synthetic construct
SEQUENCE: 23
tcggcgatct acgcagcgac atatatttag accagatctg agcctgggag ctctctggct  60
aataacaacc acttcctaat ctgtcatctt ctg                               93

SEQ ID NO: 24          moltype = RNA  length = 90
FEATURE                Location/Qualifiers
source                 1..90
                       mol_type = other RNA
                       organism = synthetic construct
SEQUENCE: 24
tcggcgatct acgcagcgac ataatactgg gtcgcagtaa ccccagttaa caaaacaagt  60
aacaaccact tcctaatctg tcatcttctg                                   90

SEQ ID NO: 25          moltype = RNA  length = 91
FEATURE                Location/Qualifiers
source                 1..91
                       mol_type = other RNA
```

-continued

```
                         organism = synthetic construct
SEQUENCE: 25
tcggcgatct acgcagcgac ataataagag gctctagcta caccctctat aaaaaactaa  60
taacaaccac ttcctaatct gtcatcttct g                                 91

SEQ ID NO: 26            moltype = RNA  length = 91
FEATURE                  Location/Qualifiers
source                   1..91
                         mol_type = other RNA
                         organism = synthetic construct
SEQUENCE: 26
tcggcgatct acgcagcgac ataataagag gttctggcta caccctctat aaaaaactaa  60
taacaaccac ttcctaatct gtcatcttct g                                 91

SEQ ID NO: 27            moltype = RNA  length = 91
FEATURE                  Location/Qualifiers
source                   1..91
                         mol_type = other RNA
                         organism = synthetic construct
SEQUENCE: 27
tcggcgatct acgcagcgac ataataagag gttctagcta taccctctat aaaaaactaa  60
taacaaccac ttcctaatct gtcatcttct g                                 91

SEQ ID NO: 28            moltype = RNA  length = 91
FEATURE                  Location/Qualifiers
source                   1..91
                         mol_type = other RNA
                         organism = synthetic construct
SEQUENCE: 28
tcggcgatct acgcagcgac ataataagag gtcctagcta taccctctat aaaaaactaa  60
taacaaccac ttcctaatct gtcatcttct g                                 91

SEQ ID NO: 29            moltype = RNA  length = 118
FEATURE                  Location/Qualifiers
source                   1..118
                         mol_type = other RNA
                         organism = synthetic construct
SEQUENCE: 29
tcggcgatct acgcagcgac atatattagc ttatcagact gatgttgact gttgaatctc  60
aatggtcaac accagtcgat gggctgttaa caaccacttc ctaatctgtc atcttctg    118

SEQ ID NO: 30            moltype = RNA  length = 93
FEATURE                  Location/Qualifiers
source                   1..93
                         mol_type = other RNA
                         organism = synthetic construct
SEQUENCE: 30
tcggcgatct acgcagcgac atatatctgc tgctgctgct gctgctgctg ctgctgctgc  60
tgtaacaacc acttcctaat ctgtcatctt ctg                               93

SEQ ID NO: 31            moltype = DNA  length = 131
FEATURE                  Location/Qualifiers
source                   1..131
                         mol_type = other DNA
                         organism = synthetic construct
SEQUENCE: 31
cagaagatga cagattagga agtggttgtt aggccctagt tagccagaga gctcccaggc  60
tcagatctgg tctaaccaga gccatatatg tcgctgcgta gatcgccgag aatctatagt  120
gagtcgtatt a                                                       131

SEQ ID NO: 32            moltype = DNA  length = 138
FEATURE                  Location/Qualifiers
source                   1..138
                         mol_type = other DNA
                         organism = synthetic construct
SEQUENCE: 32
cagaagatga cagattagga agtggttgtt aacagcccat cgactggtgt tgccatgaga  60
ttcaacagtc aacatcagtc tgataagcta atatatgtcg ctgcgtagat cgccgagaat  120
ctatagtgag tcgtatta                                                138

SEQ ID NO: 33            moltype = DNA  length = 115
FEATURE                  Location/Qualifiers
source                   1..115
                         mol_type = other DNA
                         organism = synthetic construct
SEQUENCE: 33
cagaagatga cagattagga agtggttgtt acagcagcag cagcagcagc agcagcagca  60
gcagcagata tatgtcgctg cgtagatcgc cgagaatcta tagtgagtcg tatta       115
```

-continued

```
SEQ ID NO: 34          moltype = DNA  length = 142
FEATURE                Location/Qualifiers
source                 1..142
                       mol_type = other DNA
                       organism = synthetic construct
SEQUENCE: 34
cagaagatga cagattagga agtggttgtt acagcagcag cagcagcagc agcagcagca  60
gcagcagcag cagcagcagc agcagcagca gcagatatat gtcgctgcgt agatcgccga  120
gaatctatag tgagtcgtat ta                                           142

SEQ ID NO: 35          moltype = DNA  length = 129
FEATURE                Location/Qualifiers
source                 1..129
                       mol_type = other DNA
                       organism = synthetic construct
SEQUENCE: 35
cagaagatga cagattagga agtggttgtt aggctaatga attcctttac accacactgt  60
cgtcgaatgg ccactcccag tatatatgtc gctgcgtaga tcgccgagaa tctatagtga  120
gtcgtatta                                                          129

SEQ ID NO: 36          moltype = DNA  length = 148
FEATURE                Location/Qualifiers
source                 1..148
                       mol_type = other DNA
                       organism = synthetic construct
SEQUENCE: 36
cagaagatga cagattagga agtggttgtt aaagccctgt agacgacatc agtactagtg  60
cctgtgccgc acggtgtaag acgggctgca cttacaccgc aaacccgtcg ctgcgtagat  120
cgccgagaat ctatagtgag tcgtatta                                     148

SEQ ID NO: 37          moltype = DNA  length = 148
FEATURE                Location/Qualifiers
source                 1..148
                       mol_type = other DNA
                       organism = synthetic construct
SEQUENCE: 37
cagaagatga cagattagga agtggttgtt aaagccctgt atacgacatc agtactagtg  60
cctgtgccgc acggtgtaag acgggctgca cttacaccgc aaacccgtcg ctgcgtagat  120
cgccgagaat ctatagtgag tcgtatta                                     148

SEQ ID NO: 38          moltype = DNA  length = 113
FEATURE                Location/Qualifiers
source                 1..113
                       mol_type = other DNA
                       organism = synthetic construct
SEQUENCE: 38
cagaagatga cagattagga agtggttgtt attagttttt tatagagggt gtagctagaa  60
cctctatata tgtcgctgcg tagatcgccg agaatctata gtgagtcgta tta         113

SEQ ID NO: 39          moltype = DNA  length = 112
FEATURE                Location/Qualifiers
source                 1..112
                       mol_type = other DNA
                       organism = synthetic construct
SEQUENCE: 39
cagaagatga cagattagga agtggttgtt acttgttttg ttaactgggg ttactgcgac  60
ccagatatat gtcgctgcgt agatcgccga gaatctatag tgagtcgtat ta          112

SEQ ID NO: 40          moltype = DNA  length = 142
FEATURE                Location/Qualifiers
source                 1..142
                       mol_type = other DNA
                       organism = synthetic construct
SEQUENCE: 40
cagaagatga cagattagga agtggttgtt attgtaatca ggattttacg gttcctggta  60
gacaccctca aaccatatta ttgaggttat acaaatatat gtcgctgcgt agatcgccga  120
gaatctatag tgagtcgtat ta                                           142

SEQ ID NO: 41          moltype = DNA  length = 25
FEATURE                Location/Qualifiers
source                 1..25
                       mol_type = other DNA
                       organism = synthetic construct
SEQUENCE: 41
cagaagatga cagattagga agtgg                                        25

SEQ ID NO: 42          moltype = DNA  length = 57
FEATURE                Location/Qualifiers
source                 1..57
```

-continued

```
                         mol_type = other DNA
                         organism = synthetic construct
SEQUENCE: 42
gtgtcttttg gtctttctgg tgctcttcga atcagaagat gacagattag gaagtgg     57

SEQ ID NO: 43            moltype = DNA  length = 20
FEATURE                  Location/Qualifiers
source                   1..20
                         mol_type = other DNA
                         organism = synthetic construct
SEQUENCE: 43
gtcgctgcgt agatcgccga                                              20

SEQ ID NO: 44            moltype = DNA  length = 32
FEATURE                  Location/Qualifiers
source                   1..32
                         mol_type = other DNA
                         organism = synthetic construct
SEQUENCE: 44
attcgaagag caccagaaag accaaaagac ac                                32

SEQ ID NO: 45            moltype = DNA  length = 42
FEATURE                  Location/Qualifiers
source                   1..42
                         mol_type = other DNA
                         organism = synthetic construct
SEQUENCE: 45
attcgaagag caccagaaag accaaaagac acagtcacag at                     42

SEQ ID NO: 46            moltype = DNA  length = 45
FEATURE                  Location/Qualifiers
source                   1..45
                         mol_type = other DNA
                         organism = synthetic construct
SEQUENCE: 46
attcgaagag caccagaaag accaaaagac acgacagatc gctct                  45

SEQ ID NO: 47            moltype = DNA  length = 59
FEATURE                  Location/Qualifiers
source                   1..59
                         mol_type = other DNA
                         organism = synthetic construct
modified_base            46
                         mod_base = OTHER
                         note = Bicyclooctyne modified base
SEQUENCE: 47
attcgaagag caccagaaag accaaaagac acgacagatc gctctttgag cgatctgtc   59

SEQ ID NO: 48            moltype = DNA  length = 32
FEATURE                  Location/Qualifiers
source                   1..32
                         mol_type = other DNA
                         organism = synthetic construct
SEQUENCE: 48
gtgtcttttg gtctttctgg tgctcttcga at                                32

SEQ ID NO: 49            moltype = DNA  length = 22
FEATURE                  Location/Qualifiers
source                   1..22
                         mol_type = other DNA
                         organism = synthetic construct
SEQUENCE: 49
ggagagacag atgaggagag tg                                           22

SEQ ID NO: 50            moltype = DNA  length = 54
FEATURE                  Location/Qualifiers
source                   1..54
                         mol_type = other DNA
                         organism = synthetic construct
SEQUENCE: 50
gtgtcttttg gtctttctgg tgctcttcga atggagagac agatgaggag agtg        54

SEQ ID NO: 51            moltype = DNA  length = 18
FEATURE                  Location/Qualifiers
source                   1..18
                         mol_type = other DNA
                         organism = synthetic construct
SEQUENCE: 51
taatacgact cactatag                                                18
```

-continued

```
SEQ ID NO: 52           moltype = DNA  length = 20
FEATURE                 Location/Qualifiers
source                  1..20
                        mol_type = other DNA
                        organism = synthetic construct
SEQUENCE: 52
tcggcgatct acgcagcgac                                            20

SEQ ID NO: 53           moltype = DNA  length = 25
FEATURE                 Location/Qualifiers
source                  1..25
                        mol_type = other DNA
                        organism = synthetic construct
SEQUENCE: 53
ccacttccta atctgtcatc ttctg                                      25
```